(12) United States Patent
Kibbe et al.

(10) Patent No.: US 9,801,738 B2
(45) Date of Patent: Oct. 31, 2017

(54) LIQUID CAST BIODEGRADABLE ARTERIAL STENT

(75) Inventors: Melina R. Kibbe, Chicago, IL (US); Guillermo A. Ameer, Chicago, IL (US)

(73) Assignee: Northwestern University, Evanston, IL (US)

( * ) Notice: Subject to any disclaimer, the term of this patent is extended or adjusted under 35 U.S.C. 154(b) by 539 days.

(21) Appl. No.: 13/641,378

(22) PCT Filed: Apr. 14, 2011

(86) PCT No.: PCT/US2011/032533
§ 371 (c)(1),
(2), (4) Date: Dec. 4, 2012

(87) PCT Pub. No.: WO2011/130539
PCT Pub. Date: Oct. 20, 2011

(65) Prior Publication Data
US 2013/0211500 A1    Aug. 15, 2013

Related U.S. Application Data

(60) Provisional application No. 61/323,955, filed on Apr. 14, 2010.

(51) Int. Cl.
| A61F 2/82 | (2013.01) |
| A61L 31/06 | (2006.01) |
| A61L 31/14 | (2006.01) |
| A61L 31/16 | (2006.01) |

(52) U.S. Cl.
CPC ................ *A61F 2/82* (2013.01); *A61L 31/06* (2013.01); *A61L 31/14* (2013.01); *A61L 31/148* (2013.01); *A61L 31/16* (2013.01); *A61L 2300/114* (2013.01); *A61L 2300/604* (2013.01); *A61L 2400/16* (2013.01)

(58) Field of Classification Search
CPC ..................................... A61F 2/06; A61F 2/82
USPC ......................................................... 623/1.21
See application file for complete search history.

(56) References Cited

U.S. PATENT DOCUMENTS

| 5,383,928 | A | 1/1995 | Scott et al. | |
|---|---|---|---|---|
| 6,099,730 | A | 8/2000 | Ameer et al. | |
| 6,699,470 | B1 | 3/2004 | Ameer et al. | |
| 7,097,855 | B1 | 8/2006 | Ameer et al. | |
| 7,722,894 | B2 | 5/2010 | Wang et al. | |
| 2003/0118692 | A1 | 6/2003 | Wang et al. | |
| 2005/0063939 | A1 | 3/2005 | Ameer et al. | |
| 2005/0281883 | A1* | 12/2005 | Daniloff et al. | 424/489 |
| 2006/0013855 | A1 | 1/2006 | Carpenter et al. | |
| 2006/0155178 | A1 | 7/2006 | Backman et al. | |
| 2007/0071790 | A1 | 3/2007 | Ameer et al. | |
| 2007/0142897 | A1 | 6/2007 | Consigny et al. | |
| 2007/0150047 | A1 | 6/2007 | Ruane et al. | |
| 2007/0208420 | A1 | 9/2007 | Ameer et al. | |

(Continued)

OTHER PUBLICATIONS

International Search Report for PCT/US2011/032533 dated Dec. 23, 2011.

(Continued)

*Primary Examiner* — Matthew Schall

(57) ABSTRACT

Disclosed are liquid cast biodegradable arterial stents and methods for preparing liquid cast biodegradable arterial stents. The typically includes a biodegradable polymer and may include an agent for treating neointimal hyperplasia.

10 Claims, 24 Drawing Sheets

(56) References Cited

U.S. PATENT DOCUMENTS

| | | |
|---|---|---|
| 2007/0224245 A1 | 9/2007 | Ameer et al. |
| 2009/0148945 A1 | 6/2009 | Ameer et al. |
| 2009/0325859 A1 | 12/2009 | Ameer et al. |
| 2010/0034897 A1 | 2/2010 | Ameer et al. |
| 2010/0036476 A1 | 2/2010 | Ameer et al. |
| 2010/0076162 A1 | 3/2010 | Ameer et al. |
| 2011/0071079 A1 | 3/2011 | Ameer et al. |
| 2011/0082421 A1 | 4/2011 | Ameer et al. |
| 2012/0225972 A1 | 9/2012 | Ameer et al. |
| 2012/0237443 A1 | 9/2012 | Ameer et al. |

OTHER PUBLICATIONS

Written Opinion for PCT/US2011/032533 dated Dec. 23, 2011.
International Preliminary Report on Patentability for PCT/US2011/032533 dated Oct. 26, 2012.

* cited by examiner

LIQUID CAST BIODEGRADABLE ARTERIAL STENT

CROSS REFERENCE TO RELATED APPLICATION

The present application is the U.S. national stage application of International Application PCT/US2011/032533, filed Apr. 14, 2011, which international application was published on Feb. 23, 2012, as International Publication WO2011/130539. The International Application claims priority of U.S. Provisional Application No. 61/323,955, filed Apr. 14, 2010, the contents of which are incorporated herein by reference in their entireties.

BACKGROUND

The field of the invention relates to arterial stents. In particular, the field of the invention relates to liquid cast biodegradable arterial stents and methods for preparing liquid cast biodegradable arterial stems in situ in a subject in need thereof.

In 2004, more than 1 million Americans underwent coronary angioplasty and more than 80% of these patients received an arterial stent [1]. While stent technology has improved over the years, including the development of drug-eluting stents, failure rates remain high. The high failure rate of current stent technology is secondary to the development of neointimal hyperplasia and acute arterial thrombosis. Neointimal hyperplasia develops from the exaggerated growth of vascular smooth muscle cells (VSMC) which re-occludes the lumen of the artery. Two FDA-approved drug-eluting stents using sirulimus or paclitaxel were designed to prevent this process. However, recent data have shown that drug-eluting stems are associated with higher rates of in-stent thrombosis secondary to a lack of re-endothelialization at the site of intervention. Pre-formed biodegradable stents may address some of these concerns, yet several challenges must be overcome before pre-formed biodegradable stents will be used clinically, including providing sufficient external radial force, compressibility, and elastic recoil, as well as be developed into a low profile delivery system typically no more than a few millimeters in maximum diameter.

SUMMARY

Disclosed are liquid cast biodegradable arterial stents and methods for preparing liquid cast biodegradable arterial stents. Typically, the liquid cast biodegradable arterial stents include a biodegradable polymer and may include an agent for treating neointimal hyperplasia.

The biodegradable polymer may be formed from a prepolymer, for example, by cross-linking a prepolymer solution. In some embodiments, the prepolymer is formed by reacting a mixture comprising a tricarboxylic acid and an alkane diol. The prepolymer thus formed may be reacted with a compound having a crosslinkable group (e.g., an amine group or an acrylate group) in order to functionalize the prepolymer. Suitable tricarboxylic acids for preparing the prepolymer may include citric acid. Suitable alkane diols for preparing the polymer may include alkane diols having the formula OH—$(CH_2)_n$—OH where n is 6-14 (e.g., 1,8-octanediol, and 1,12-dodecanediol).

Suitable functionalizing compounds having crosslinkable groups include dihydroxy amine compounds (e.g., N,N-bis (2-hydroxyethyl)-ethylene diamine). Other suitable functionalizing compounds having crosslinkable groups include compounds that introduce acrylate groups, which may include substituted alkyl prop-2-enoate compounds. For example, the prepolymer may be reacted with an amino-substituted alkyl prop-2-enoate compound in order to provide a prepolymer that is functionalized at one or more hydroxyl groups with an acrylate group. The prepolymer may be cross-linked (e.g., via the functional groups) to form the biodegradable polymer. Suitable treatments for initiating polymerization and/or cross-linking include reacting the prepolymer with a compound that generates NO and/or exposing the prepolymer to light (e.g., UV light or visible light).

The liquid cast stent disclosed herein preferably has desirable physical and mechanical characteristics after casting in vivo and prior to biodegradation. Preferably, the stent has a suitable radial strength, a suitable axial strength, a suitable resistance to elastic deformation, a suitable flexibility, a suitable Young's modulus, and a suitable resistance to fracture. The physical and mechanical characteristics of the liquid cast stent may mimic those characteristics of a healthy artery. The mechanical properties of arteries in vivo have been studied in the art. (See Peterson et al., "Mechanical Properties in vivo," Circulation Research, Volume VIII, May 1960, 622-639, the content of which is incorporated herein by reference in its entirety.) Likewise, the physical and mechanical characteristics of the liquid cast stent may mimic or differ from those characteristics of typical metal stents. The physical and mechanical properties of a typical metal stent may be defined as follows: (a) the stent has a radial strength of about 2-6 N at a strain of about 0.5; (b) the stent tolerates an axial force up to about 30%; (c) the stem tolerates elastic deformation of up to about 80%; (d) the stent has a flexibility of about 0.5-150×10-2 N per degree flexion; and (e) the stent has a Young's modulus of about 50 Pa to about 200 Pa.

Preferably, the liquid cast stents disclosed herein exhibit a low fracture rate after casting in vivo and prior to biodegradation. In some embodiments, the liquid cast stents have a fracture rate of less than about 2% (more preferably less than about 1%, and most preferably 0%).

The stent may comprise or release one or more agents for treating atherosclerosis, thrombosis, or neointimal hyperplasia. In some embodiments, the stent comprises and/or releases NO. For example, the prepolymer may be exposed to NO gas (e.g., prior to, concurrently with, or after cross-linking) to form a diazeniumdiolate NO donor. In some embodiments, the stent releases NO at a rate of at least about 10 nmol/24 hr/mm$^2$ (preferably at least about 20 nmol/24 hr/mm$^2$, more preferably at least about 30 nmol/24 hr/mm$^2$). Preferably, the stent releases a drug or small molecule for at least 1-30 days or longer (e.g., for at least about 10 days (preferably at least about 20 days, more preferably for at least about 30 days)). In some embodiments, the stent releases NO with a half-life of approximately 7 days.

The stent may comprise one or more agents that modify one or more physical properties. For example, the stent may comprise one or more agents that modify the stent's adhesion to arterial vessels such as a polypeptide comprising at least a fragment of the amino acid sequence of human transglutaminase (GenBank Accession No. BAA14329, e.g., at least about 10 contiguous amino acids of human transglutaminase, or preferably at least about 20, 30, 40, 50, 100, 200, 300, 400, 500, 600, 700, or the full-length 817 amino acid sequence).

The disclosed stent may be formed in a subject in need thereof by a method that includes: (a) introducing a prepolymer solution to the subject at a site of stent formation; and (b) curing the prepolymer solution (e.g., via polymerizing and/or cross-linking) to form the stent. Curing may be initiated or promoted by applying heat or light (e.g. UV light or visible light) to the prepolymer solution. As such, the methods contemplated herein may include (a) introducing a prepolymer solution to the subject at a site of stent formation; and (b) applying heat or light to the prepolymer solution to form the stent. In some embodiments, the methods contemplated herein may include one or more of the following steps: (a) delivering a triple balloon catheter to a site of interest in a patient in need thereof; (b) inflating occlusion balloons of the catheter; (c) irrigating space between the occlusion balloons; (d) injecting a polymer into the space between the balloons; inflating an inner molding balloon between the occlusion balloons; (e) polymerizing the stent by subjecting the polymer to light or heat; (f) deflating the inner molding balloon; (g) irrigating the space between the occlusion balloons to remove any non-polymerized polymer; and (h) deflating the occlusion balloons and removing the catheter.

The prepolymer solution comprises the prepolymer in a suitable solvent. Suitable solvents include water and mixtures of water:ethanol. In some embodiments, the prepolymer solution comprises 10-80 wt % prepolymer (preferably 15-70% prepolymer, more preferably 20-60 wt % prepolymer) and has a viscosity of about 0.5-70 cp (preferably about 1-60 cp, more preferably about 2-50 cp). In the methods, cross-linking may be initiated by adding a radical initiator to the prepolymer solution, optionally at a concentration of no more than about 2% of the prepolymer content of the solution (preferably no more than about 1% of the prepolymer content of the solution, more preferably no more than about 0.5% of the prepolymer content of the solution).

DETAILED DESCRIPTION

Figure 1:
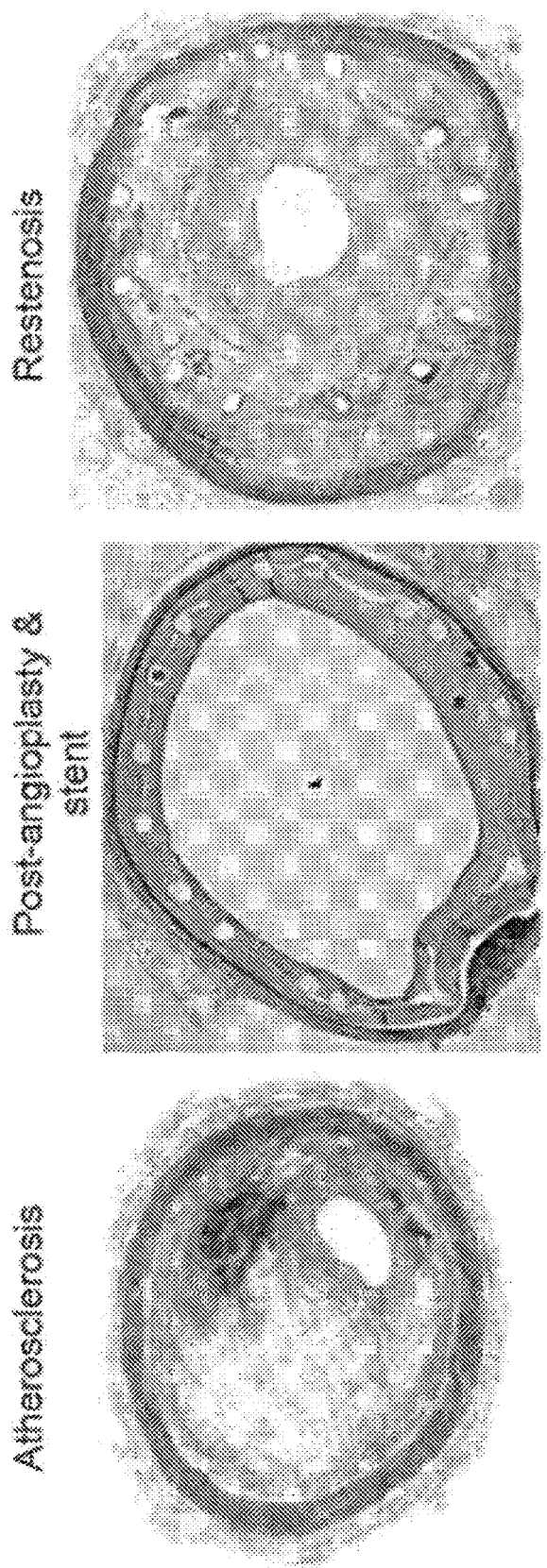
FIG. 1 illustrates development of restenosis from neointimal hyperplasia following balloon angioplasty and stent placement.

The disclosed subject matter further may be described utilizing terms as defined below.

Unless otherwise specified or indicated by context, the terms "a", "an", and "the" mean "one or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising."

The terms "patient" and "subject" may be used interchangeably herein. A patient may be a human patient.

A "patient in need thereof" may refer to a patient having or at risk for acquiring an arterial disease or disorder such as atherosclerosis. A patient in need thereof may refer to a patient having or at risk for acquiring neointimal hyperplasia or acute arterial thrombosis. A patient in need thereof may refer to a patient having recently undergone an angioplasty procedure.

As used herein, "biodegradable" describes a material, such as a polymer, that is capable of being degraded in a physiological environment into smaller basic components. Preferably, the smaller basic components are innocuous. For example, an biodegradable polymer may be degraded into basic components that include, but are not limited to, water, carbon dioxide, sugars, organic acids (e.g., tricarboxylic or amino acids), and alcohols (e.g., glycerol or polyethylene glycol). Biodegradable materials (including polymers) that may be utilized to prepare the stems contemplated herein may include materials disclosed in U.S. Pat. Nos. 7,470,283; 7,390,333; 7,128,755; 7,094,260; 6,830,747; 6,709,452; 6,699,272; 6,527,801; 5,980,551; 5,788,979; 5,766,710; 5,670,161; and 5,443,458; and U.S. Published Application Nos. 20090319041; 20090299465; 20090232863; 20090192588; 20090182415; 20090182404; 20090171455; 20090149568; 20090117039; 20090110713; 20090105352; 20090082853; 20090081270; 20090004243; 20080249633; 20080243240; 20080233169; 20080233168; 20080220048; 20080154351; 20080152690; 20080119927; 20080103583; 20080091262; 20080071357; 20080069858; 20080051880; 20080008735; 20070298066; 20070288088; 20070287987; 20070281117; 20070275033; 20070264307; 20070237803; 20070224247; 20070224244; 20070224234; 20070219626; 20070203564; 20070196423; 20070141100; 20070129793; 20070129790; 20070123973; 20070106371; 20070050018; 20070043434; 20070043433; 20070014831; 20070005130; 20060287710; 20060286138; 20060264531; 20060198868; 20060193892; 20060147491; 20060051394; 20060018948; 20060009839; 20060002979; 20050283224; 20050278015; 20050267565; 20050232971; 20050177246; 20050169968; 20050019404; 20050010280; 20040260386; 20040230316; 20030153972; 20030153971; 20030144730; 20030118692; 20030109647; 20030105518; 20030105245; 20030097173; 20030045924; 20030027940; 20020183830; 20020143388; 20020082610; and 0020019661; the contents of which are incorporated herein by reference in their entireties.

Suitable biodegradable polymers that may be utilized to prepare the stents contemplated herein may include those disclosed in U.S. Published Application No. 20100076162, the content of which is incorporated herein by reference in its entirety. Suitable prepolymers for forming the polymers contemplated herein may be formed from carboxylic acids and alkane diol precursors. For example, prepolymers may be formed from tricarboxylic acids, such as citric acid, and alkane diols, such as alkane diols having the formula OH—$(CH_2)_n$—OH where n is 6-14 (e.g., 1,8-octanediol). Polymers contemplated herein may be formed from prepolymers such as poly(1,8 octanediol-co-citric acid) (aka "POC"), poly(1,10-Decanediol-Co-Citric Acid) (aka "PDC"), and poly(1,12-dodecanediol-co-citric acid) (aka "PDDC") which optionally may be functionalized at one or more positions (e.g., with an amino group or an acrylate group).

The liquid cast polymer stents may be formed by subjecting a prepolymer solution to heat and/or light (e.g., UV light or visible light). Heat and/or light may be utilized to facilitate curing of the prepolymer solution (e.g. via polymerization and/or crosslinking). Optionally, the prepolymers may be functionalized at one or more positions. For example, the prepolymers may be functionalized at one or more hydroxyl positions via reacting the prepolymer with a reagent that provides a crosslinkable amine group or a crosslinkable acrylate group. Optionally, the prepolymer solution comprises a crosslinking initiator compound.

Suitable light for forming the liquid cast polymer stents may include UV light and or visible light. UV light may include Ultraviolet A, long wave, or black light, abbreviated "UVA" and having a wavelength of 400 nm-315 nm; Near UV light, abbreviated "NUV" and having a wavelength of 400 nm-300 nm; Ultraviolet B or medium wave, abbreviated "UVB" and having a wavelength of 315 nm-280 nm; Middle UV light, abbreviated "MUV" and having a wavelength of 300 nm-200 nm; Ultraviolet C, short wave, or germicidal, abbreviated "UVC" and having a wavelength of 280 nm-100 nm; Far UV light, abbreviated "FUV" and having a wavelength of 200 nm-122 nm; Vacuum UV light, abbreviated "VUV" and having a wavelength of 200 nm-100 nm; Low UV light, abbreviated "LUV" and having a wavelength of 100 nm-88 nm; Super UV light, abbreviated "SUV" and having a wavelength of 150 nm-10 nm; and Extreme UV light, abbreviated "EUV" and having a wavelength of 121 nm-10 nm. Visible light may include violet light having a wavelength of 380-450 nm; blue light having a wavelength of 450-475 nm; cyan light having a wavelength of 476-495 nm; green light having a wavelength of 495-570 nm; yellow light having a wavelength of 570-590 nm; orange light having a wavelength of 590-620 nm; and red light having a wavelength of 620-750 nm. In some embodiments, light utilized in the presently disclosed methods has a wavelength between about 300 nm and 500 nm. Suitable light for curing the prepolymer solution may include blue light having a wavelength between about 450-475 nm.

Atherosclerosis.

The presently disclosed subject matter relates to atherosclerosis. Atherosclerosis is prevalent in all developed nations and is the leading cause of death and disability in the United States. Deaths due to cardiovascular disease account for 2,400 deaths per day, or 871,517 deaths per year, more than the next five leading causes of death combined [1]. Seventy-nine million Americans currently have cardiovascular disease and it is estimated that this number will increase significantly due to the growth of the aging population [1]. Furthermore, it is estimated that $432 billion per year is spent in the United States on cardiovascular disease, with a significant portion being attributed to the cost of repeat interventions [1]. One of the current therapeutic modalities for severe arterial atherosclerosis, whether it is from coronary or peripheral arterial disease, consists of balloon angioplasty and stenting (See FIG. 1). Unfortunately, the long-term durability of this procedure is limited due to the development of neointimal hyperplasia, which results from an aggressive growth of the smooth muscle cells that line the arterial wall. For example, approximately 31-46% of balloon angioplasty sites develop angiographic restenosis at 6 months [1, 2]. Arterial stents and new anti-platelet agents have reduced the 1-year angiographic restenosis rate to 27% [3]. By two years, 20% of patients require repeat balloon angioplasty [4]. Drug-eluting stents have slightly reduced the need for re-intervention [5]. However, long-term data is now suggesting equal or higher mortality rates with drug-eluting stents compared to bare-metal stents [5, 6]. Moreover, the recent COURAGE trial reported that 21% of patients who underwent balloon angioplasty and stenting still required subsequent revascularization within a median time of 10 months [7]. Thus, neointimal hyperplasia is an alarming problem that causes significant morbidity and mortality. Currently, no effective therapeutic modality exists to prevent the development of neointimal hyperplasia.

Arterial Injury Response and the Development of Neointimal Hyperplasia.

The response of the artery to balloon injury has been well described by Clowes et al. [8] Balloon inflation, while designed to be therapeutic, actually causes endothelial cell injury, and with extreme inflation the internal elastic lamina is fractured, thereby exposing the underlying VSMC to circulating blood elements. Platelets immediately aggregate and adhere to the site of injury and an inflammatory response follows, with infiltration of macrophages and leukocytes [9, 11]. The platelets, inflammatory cells, and injured VSMC secrete a variety of growth factors and cytokines, such as basic fibroblast growth factor (bFGF), platelet-derived growth factor, endothelin, and angiotensin II, that stimulate the VSMC to proliferate and migrate to the subintima [9, 12, 14]. Concurrently, endothelial cell regeneration occurs through the stimulation of bFGF within 24 hours after injury and continues for 6-10 weeks [15]. Lastly, transforming growth factor-β stimulates a marked upregulation in the genes that encode for extracellular matrix proteins, such as procollagen, collagen, and proteoglycans with deposition of matrix [16, 17]. The culmination of all of these events results in a significant accumulation of cells and matrix within the neointima that ultimately re-occludes the vessel.

Role of NO in the Vasculature.

One promising therapeutic strategy to prevent neointimal hyperplasia has centered on the use of NO, a molecule normally produced in endothelial cells that serves to protect the vessel wall. It is a small, diffusible molecule with a very short half-life that is produced from L-arginine by one of three different enzymes, endothelial nitric oxide synthase (eNOS), neuronal nitric oxide synthase (nNOS), or inducible nitric oxide synthase (iNOS). While these isoforms share a number of similarities, they are also clearly distinct. They all require the cofactors NADPH, FAD, FMN, heme, and tetrahydrobiopterin to catalyze the reaction [18]. But, in general, eNOS and nNOS are constitutively expressed enzymes and NO production is regulated predominantly by intracellular $Ca^{2+}$ fluxes that permit calmodulin binding which activates the enzymes [18]. Vaughn et al. reported that resting endothelial cells in the vasculature constitutively release ~4 $pmol/min/mm^2$, which equals 5.8 $nmol/24$ $hr/mm^2$ [19]. In contrast to eNOS and nNOS, iNOS is transcriptionally regulated and is not normally produced by most cells. Typically, iNOS expression in response to cellular stress generates ~100-fold more NO than its constitutive counterparts whose roles are involved in physiological regulations [18].

NO has been shown to possess many different vasoprotective properties, including inhibition of platelet aggregation [20], leukocyte adherence [21], VSMC proliferation [22, 23], VSMC migration [23], stimulation of VSMC apoptosis [24], and endothelial cell growth [25]. NO is also a potent vasodilator [26, 27]. All of these properties of NO serve to maintain vascular homeostasis by affecting all the key components in the injury response. Hence, the loss of NO secondary to endothelial cell denudation following vascular injury is pivotal to the development of neointimal hyperplasia.

NO Delivery to the Vasculature.

Since the normal source of NO is lost following vascular injury due to denudation of the endothelial cells, if NO were restored at the site of injury, the development of neointimal hyperplasia should be prevented. Indeed, many investigators have shown that supplementation of NO at the site of injury prevents the development of neointimal hyperplasia. These forms of NO-based approaches have included systemic delivery of L-arginine or NO donors, inhalational NO, local application of NO donors, and gene therapy of one of the NOS enzymes [26-38]. Previous work by the principal investigator (PI) has shown that PROLI/NO, a short-acting NO donor, inhibited the development of neointimal hyperplasia by 91% when applied to the periadventitial aspect of an injured artery [39]. Furthermore, a NO-releasing nanoparticle gel also effectively inhibited the development of neointimal hyperplasia following arterial injury and stimulated reformation of an intact endothelial cell layer [40]. Using an alternative approach, Fishbein et al. fabricated NO-releasing stainless steel stents and demonstrated that NO release from the stents inhibited neointimal hyperplasia by 50% [41]. These two approaches, i.e. periadventitial application versus luminal delivery, while very different, were both effective. This demonstrates the highly diffusible nature of NO, thereby allowing the NO to permeate throughout all layers of the arterial wall to impart its overall effect. These studies support the highly effective nature of NO at inhibiting neointimal hyperplasia as well as the feasibility of an intralumenal stent-based delivery approach.

Diazeniumdiolate NO Donors.

Figure 2:
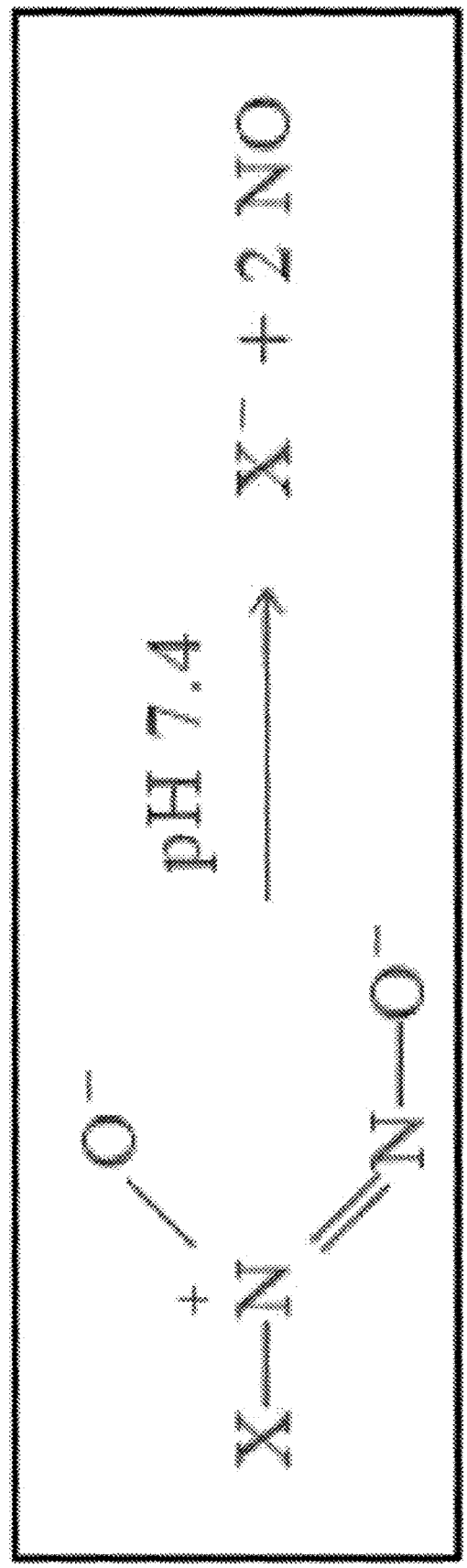
FIG. 2 illustrates diazeniumdiolate dissociation.

Diazeniumdiolate NO donors, often referred to as NONOates, are chemical species containing the [N(O)NO]-functional group that have unique characteristics that make them suitable choices for medical applications (FIG. 2). The advantages of diazeniumdiolates over other NO donors include: known predictable rates of NO-release; spontaneity of NO generation; and tunable generation of NO redox forms [42]. The most attractive of these features for medical purposes is that diazeniumdiolate NO donors dissociate spontaneously under physiological conditions (i.e., 37° C., pH 7.4) [42]. They do not require light or other initiators to release NO, just an aqueous environment. Thus, once a diazeniumdiolate is exposed to circulating blood, the hydrogen ions immediately catalyze release of NO that follows first order kinetics. Members of this class of NO donors have been successfully incorporated into synthetic polymeric materials, including biofilms, graft coatings, stent coatings, coatings for oxygen sensors, and extracorporeal circuits [25, 28, 43-38]. All of these approaches have shown extended NO release, varying from days to months, and have demonstrated biologic effects such as inhibition of thrombus formation and VSMC proliferation in vivo or in vitro. Thus, use of NO-based polymeric therapeutics in the vasculature to inhibit the development of neointimal hyperplasia provides a robust tool for the treatment of restenosis.

Drug-Eluting Stems.

In an attempt to reduce the high rate of restenosis following balloon angioplasty and stenting, drug-eluting stents were developed. The two FDA-approved drug-eluting stents are Cordis' sirulimus-eluting Cypher stent and Boston Scientific's paclitaxel-eluting Taxus stent. While early data were encouraging and demonstrated reduced rates of restenosis and late lumen loss, late results have recently been disappointing [49]. Several pooled or meta-analysis studies have revealed either similar mortality or worse mortality of these drug-eluting stents compared to bare-metal stents [50, 51]. This increased mortality appears to be secondary to an increased rate of in-stent thrombosis [52]. The drug-eluting stents, while inhibiting VSMC proliferation, are also inhibiting endothelial cell proliferation. As a result, the stem is not covered by endothelial cells and remains thrombogenic. Furthermore, Virmani's group recently demonstrated the non-uniformity of healing with drug-eluting stents. The loading dose of the drug varies from strut to strut and the variance in distance between struts exaggerates this heterogeneity, leading to more problems with healing [53]. Therefore, enthusiasm for these two FDA-approved stents has dampened significantly in the past several months and researchers are actively searching for alternatives to combat this problem.

Pre-Formed Biodegradable Stents.

Liquid cast biodegradable arterial stents formed by the presently disclosed catheters have advantageous properties over pre-formed biodegradable stents. The long-term need for stent support following balloon angioplasty has never been demonstrated. Stents are used following angioplasty to prevent elastic recoil. Thus, a stent may be required for only a short duration. Pre-formed biodegradable stents attempt to address this issue. But given that the development of these stents is in its infancy, many challenges remain. The ideal biodegradable stent should include sufficient physical support, acceptable biocompatibility profile, safe degradation characteristics, ease of use, be simple to manufacture and sterilize, and be cost-efficient. With respect to physical characteristics, the stent must have sufficient external radial strength to resist compressive forces, maintain self expandability, have low elastic recoil, and be able to anchor itself to the surrounding tissue. In addition, the pre-formed stent must be designed so that it can be collapsed into a delivery device with a small profile (2-3 millimeters). Finally, the delivery device must be flexible in order to negotiate curves during the delivery process. To date, no pre-formed biodegradable stent has been developed that meets all of these criteria.

Figure 3:
FIG. 3 illustrates an Igaki-Tamai stent, which is a premounted, balloon-expandable poly-L-lactide ("PLLA") stent.

A few biodegradable stems with some of these qualities have been fabricated and placed in humans. The first biodegradable stent was developed at Duke in the early 1980s and was made from woven poly-L-lactic acid (PLLA) polymer strands [54]. However, the first biodegradable stent implanted into humans was the Igaki-Tamai stent, which has a zig-zag helical coil design also made from PLLA (FIG. 3) [55]. Since then, several other investigators have designed stems using polyglycolic acid/poly(lactide-co-glycolide), polycaprolactone, polyhydroxy butyrate valerate, polyorthoester, and polyethyleneoxide/poly(butylene terephthalate), poly(ethylene amide) [56]. Unfortunately, most of these materials induced some degree of inflammation when implanted in animal models [57]. Three other biodegradable stents have shown some promise. These include the poly (ethylene amide) stent designed by MediVas, the BVS stent fabricated from PLLA by Guidant, and the REVA stent made of a tyrosine-derived polycarbonate material by REVA Medical. These stents must undergo more rigorous evaluation before they can be used. Hence, much work remains to be done before pre-formed biodegradable stents can be used clinically.

Liquid Biodegradable Stents.

The present inventors are unaware of any reports of liquid-formed stents in the literature. Given all of the challenges that pre-formed biodegradable stents face, it is unclear whether preformed biodegradable steins could ever replace bare-metal and drug-eluting stents. What is needed following angioplasty is a material that can provide external radial force to resist recoil, inhibit thrombosis, inhibit neointimal hyperplasia, stimulate re-endothelialization, be biodegradable, thereby allowing for complete healing of the arterial site, and be easy and inexpensive to manufacture, deliver, and use. Disclosed herein are attempts to design and evaluate a therapy that meets all of these criteria.

Disclosed herein are stems unlike any other stent that has been used in the healthcare arena. The presently disclosed stents are formed in a patient's body from a liquid phase. One suitable prepolymer for forming such stents is POC [58]. POC is a citric acid-based biodegradable elastomeric polymer and has been shown to be biocompatible in vitro and in vivo [58, 59]. This stent will polymerize and be cast into the shape of the arterial lumen with the aide of mild heat or light. This material will coat the arterial surface at the site of angioplasty, thereby providing strength as well as surface area coverage. The strength of POC can be easily manipulated by varying the degree of acrylation, thereby providing optimal strength and compliance for the vessel. This material may be diazeniumdiolated to spontaneously release a drug, NO, which will inhibit thrombosis as well as the formation of neointimal hyperplasia while simultaneously stimulating re-endothelialization. Lastly, this material will completely degrade over time, leaving a pristine healthy arterial surface in approximately 6 months. This liquid stent should be easy to fabricate and use and should be very cost-efficient. Therefore, this new technology aims to change the way arterial stenting is approached by dramatically changing the concept of what a stent should be.

To the best of the present inventors' knowledge, disclosed herein are the first attempts to create a stem that forms in the body and is tailored to the patient's individual arterial anatomy. This form of designer medicine is radically different from all other approaches currently utilized in the clinical arena. While biodegradable stents may represent one possible solution to the problems with bare-metal and drug-eluting stems, many challenges exist for the fabrication and delivery of these devices. Disclosed herein are methods to form a stent in situ from a liquid NO-releasing elastomeric polymer. Ideally, the stent will be 1) simple to manufacture, 2) cost-effective, 3) easy to use, 4) biodegradable over time, 5) completely coat the entire arterial surface thereby providing the greatest antithrombotic protection to the artery, 6) offer a high stent-to-artery surface area ratio, thus increasing the area of contact of a drug to the arterial wall (such as NO, which optionally is present in the elastomeric polymer) and increasing the therapeutic effects, and 7) will provide physical characteristics ideal for the vasculature (i.e., compliance, compressibility, elasticity, etc). Also, a benefit of this approach is that compliance of the vessel may be modulated by altering the acrylation of the polymer, which is a significant advance over current technology. This will allow design and development of a stent that has ideal compliance with the native tissue, that resists external compression, and that has sufficient elastic recoil. In fact, one of the shortcomings of preformed biodegradable stents is that they are fabricated with an open cell matrix design. The presently proposed design with polymeric material limits the compression strength preformed biodegradable stents can achieve. An advantage of the proposed technology is that the entire surface of the artery may be coated, thereby providing greater compression strength to withstand the elastic recoil that occurs following arterial injury. Furthermore, where the stent comprises NO and POC, both the NO and the POC inhibit platelets and stimulate endothelial cell growth. As such, the proposed liquid cast stent will overcome the shortcomings of current drug-eluting stents. Lastly, because the proposed biocompatible stent will degrade over time, no foreign material will be left in the artery. This concept, i.e. formation of a stem from a liquid material in the body, is a dramatic departure from current therapies and will change current thought about promoting arterial health following vascular interventions. Furthermore, the disclosed approach should have a large impact on the healthcare system, given the broad prevalence of cardiovascular disease.

ILLUSTRATIVE EMBODIMENTS

The following embodiments are illustrative and are not intended to limit the scope of the disclosed and claimed subject matter.

Embodiment 1

A liquid cast biodegradable arterial stent.

Embodiment 2

The stent of embodiment 1, wherein the stent comprises a biodegradable polymer.

Embodiment 3

The stent of embodiment 1 or 2, wherein the stent is formed by curing a solution in situ by applying light or applying heat to the solution, and the solution comprises prepolymers (e.g., POC or PDDC) or monomers (e.g., tricarboxylic acids and alkane diols) that polymerize to form the biodegradable polymer.

Embodiment 4

The stent of any of embodiments 1-3, wherein the stent comprises an agent for inhibiting neointimal hyperplasia or thrombosis.

Embodiment 5

The stem of any of embodiments 1-4, wherein the biodegradable polymer is formed from a prepolymer formed by reacting a mixture comprising a tricarboxylic acid and an alkane diol, and optionally, the prepolymer is functionalized via reaction with a dihydroxy amine compound or a substituted alkyl prop-2-enoate compound.

Embodiment 6

The stent of embodiment 5, wherein the tricarboxylic acid is citric acid.

Embodiment 7

The stem of embodiment 5, wherein the alkane diol is 1,8-octanediol.

Embodiment 8

The stem of embodiment 5, wherein the dihydroxy amine compound is N,N-bis(2-hydroxyethyl)-ethylene diamine and the substituted alkyl prop-2-enoate compound is 2-amino ethyl prop-2-enoate.

Embodiment 9

The stem of embodiment 5, wherein the prepolymer further is functionalized at one or more hydroxyl groups with an acrylate group.

Embodiment 10

The stem of embodiment 5, wherein the biodegradable polymer is formed by subjecting the prepolymer to polymerizing and/or cross-linking.

Embodiment 11

The stent of embodiment 10, wherein the polymerizing and/or cross-linking is achieved by exposing the prepolymer to heat, UV light, or visible light.

Embodiment 12

The stent of embodiment 10 or 11, wherein after polymerizing and/or cross-linking the prepolymer is exposed to NO gas.

Embodiment 13

The stem of any of embodiments 1-12, wherein the stent releases an agent that inhibits neointimal hyperplasia or thrombosis.

Embodiment 14

The stent of embodiment 13, wherein the agent is NO.

Embodiment 15

The stent of embodiment 14, wherein the stent releases NO at a rate of at least about 10 nmol/24 hr/mm$^2$ (preferably at least about 20 nmol/24 hr/mm$^2$, more preferably at least about 30 nmol/24 hr/min$^2$).

Embodiment 16

The stent of embodiment 14, wherein the stent releases NO for at least about 10 days (preferably at least about 20 days, more preferably for at least about 30 days).

Embodiment 17

The stent of embodiment 14, wherein the stent releases NO with a half-life of approximately 7 days.

Embodiment 18

The stent of claim 2, wherein the stent is formed in vivo by administering a prepolymer solution and polymerizing and/or cross-linking the prepolymer to form the biodegradable polymer.

Embodiment 19

The stent of embodiment 18, wherein the prepolymer solution comprises 10-80 wt % prepolymer (preferably 15-70% prepolymer, more preferably 20-60 wt % prepolymer) and has a viscosity of about 0.5-70 cp (preferably about 1-60 cp, more preferably about 2-50 cp).

Embodiment 20

The stent of embodiment 18, wherein the prepolymer solution comprises water or a water/ethanol mixture as a solvent for the prepolymer.

Embodiment 21

The stem of embodiment 18, wherein cross-linking is initiated by adding a radical initiator, optionally at a concentration of no more than about 2% of the prepolymer content of the solution (preferably no more than about 1% of the prepolymer content of the solution, more preferably no more than about 0.5% of the prepolymer content of the solution).

Embodiment 22

The stein of embodiment 18, wherein a 30 wt % dilution of the prepolymer has a viscosity of approximately 2-50 cp.

Embodiment 23

The stent of embodiment 1, wherein the stent comprises a polypeptide comprises at least a 10 contiguous amino acid sequence of human transglutaminase.

Embodiment 24

A method for forming a biodegradable stent in a subject in need thereof, the method comprising: (a) introducing a prepolymer solution to the subject at a site of stent formation; and (b) polymerizing and/or cross-linking the prepolymer solution to form the stent.

Embodiment 25

The method of embodiment 30, wherein the stent comprises an agent for treating thrombosis or neointimal hyperplasia.

Embodiment 26

The method of embodiment 24 or 25, wherein the prepolymer is formed by reacting a mixture comprising a tricarboxylic acid, an alkane diol, and a dihydroxy amine compound.

Embodiment 27

The method of embodiment 26, wherein the tricarboxylic acid is citric acid.

Embodiment 28

The method of embodiment 26, wherein the alkane diol is 1,8-octanediol.

Embodiment 29

The method of embodiment 26, wherein the dihydroxy amine compound is N,N-bis(2-hydroxyethyl)-ethylene diamine.

Embodiment 30

The method of any of embodiments 24-29, wherein the prepolymer further is functionalized at one or more hydroxyl groups with an acrylate group.

Embodiment 31

The method of any of embodiments 24-30, wherein the biodegradable polymer is formed by subjecting the prepolymer to polymerizing and/or cross-linking.

Embodiment 32

The method of embodiment 31, wherein the polymerizing and/or cross-linking is achieved by exposing the prepolymer to heat or UV light or visible light.

Embodiment 33

The method of embodiment 31 or 32, wherein after polymerizing and/or cross-linking the prepolymer is exposed to NO gas.

Embodiment 34

The method of any of embodiments 24-33, wherein the stent releases NO.

Embodiment 35

The method of claim 34, wherein the stent releases NO at a rate of at least about 10 nmol/24 hr/mm$^2$ (preferably at least about 20 nmol/24 hr/mm$^2$, more preferably at least about 30 nmol/24 hr/mm$^2$).

Embodiment 36

The method of embodiment 34 or 35, wherein the stent releases NO for at least about 10 days (preferably at least about 20 days, more preferably for at least about 30 days).

Embodiment 37

The method of any of embodiments 34-36, wherein the stent releases NO with a half-life of approximately 7 days.

Embodiment 38

The method of any of embodiment 24-37, wherein the prepolymer solution comprises about 10-80% wt. prepolymer (preferably about 15-70% wt. prepolymer, more preferably about 20-60% wt. prepolymer) and has a viscosity of about 0.5-70 cp (preferably about 1-60 cp, more preferably about 2-50 cp).

Embodiment 39

The method of any of embodiments 24-38, wherein the prepolymer solution comprises water or a water/ethanol mixture as a solvent for the prepolymer.

Embodiment 40

The method of embodiment 31, wherein cross-linking is initiated by adding a radical initiator, optionally at a concentration of no more than about 2% of the prepolymer content of the solution (preferably no more than about 1% of the prepolymer content of the solution, more preferably no more than about 0.5% of the prepolymer content of the solution).

EXAMPLES

The following examples are illustrative and are not intended to limit the scope of the disclosed and claimed subject matter.

Example 1

Results

NO Inhibits Neointimal Hyperplasia Following Balloon Arterial Injury.

Figure 4:
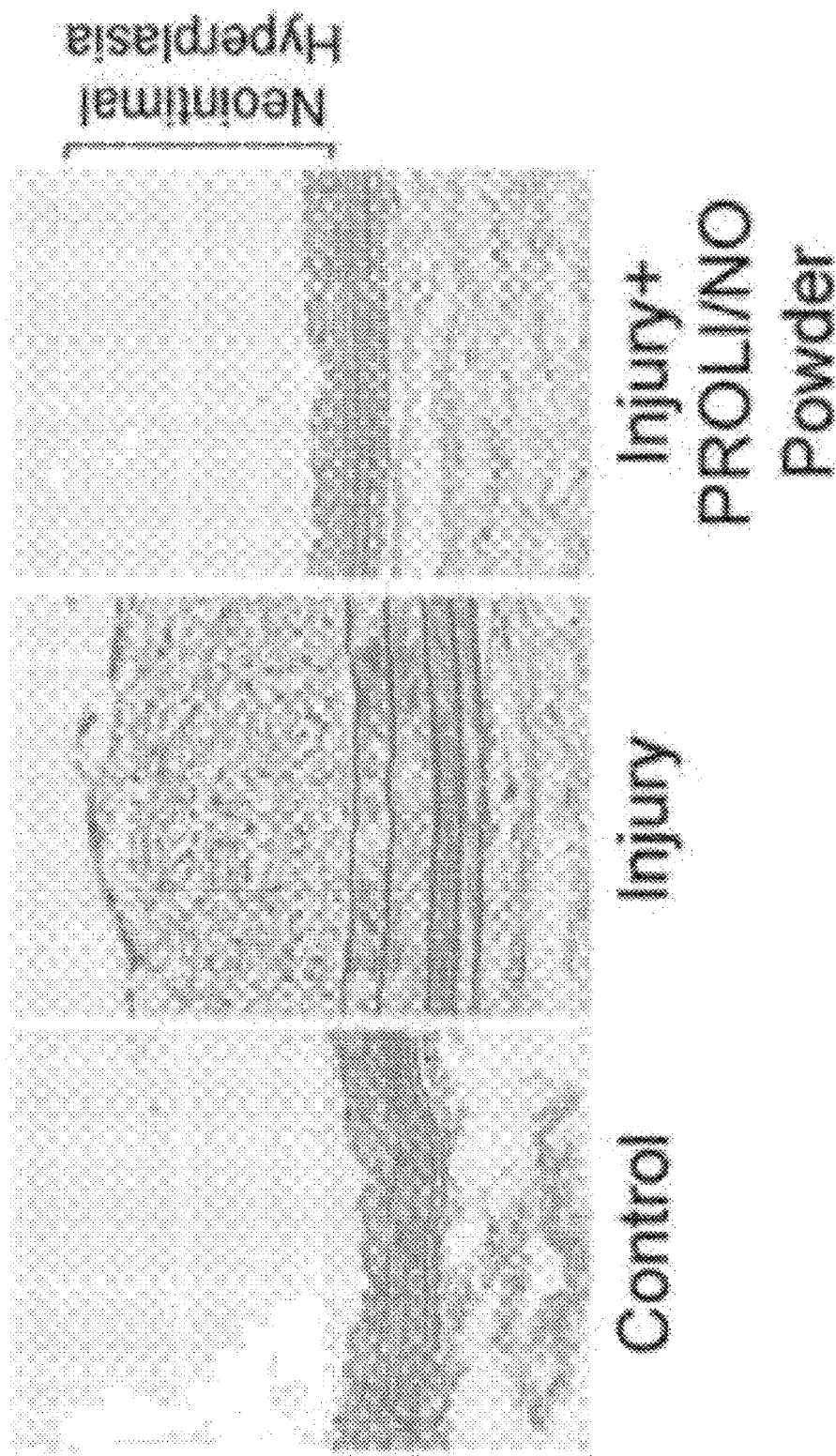
FIG. 4 illustrates that 1-[2-(carboxylato)pyrrolidin-1-yl] diazen-1-ium-1,2-diolate ("PROLI/NO") inhibits the development of neointimal hyperplasia following arterial balloon injury in rats.

Using the standard rat carotid artery injury model, the efficacy of two different diazeniumdiolates with markedly different half-lives at inhibiting neointimal hyperplasia were evaluated. These results have been published [39]. The two different NO donors investigated were: 1-[2-(carboxylato) pyrrolidin-1-yl]diazen-1-ium-1,2-diolate (PROLI/NO), a short half-life donor, and diazeniumdiolated poly(acrylonitrile) (PAN/NO), a long half-life donor. Two weeks after injury, both NO-eluting therapies successfully reduced neointimal hyperplasia. However, PROLI/NO most dramatically inhibited intimal area by 91.2% (FIG. 4) versus injury alone ($p<0.05$), whereas PAN/NO inhibited intimal area by 67% ($p<0.05$). Thus, NO-based therapies have the clinical potential to dramatically inhibit the development of neointimal hyperplasia following vascular injury.

POC is Biocompatible in the Vasculature.

Figure 5:
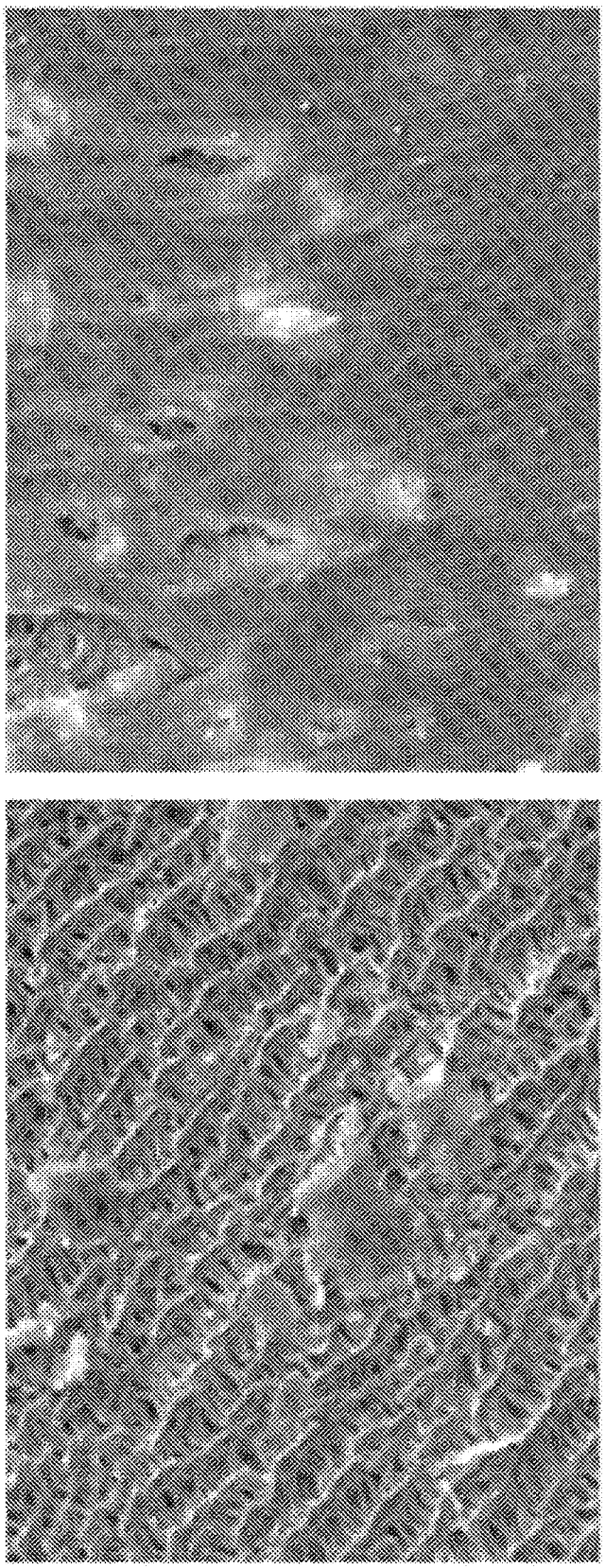
FIG. 5 illustrates SEM of human aortic endothelial cell growth on control e-polytetrafluoroethylene ("ePTFE") (left) and poly(1,8 octanediol-co-citric acid) ("POC")-ePTFE (right) grafts.
Figure 6:
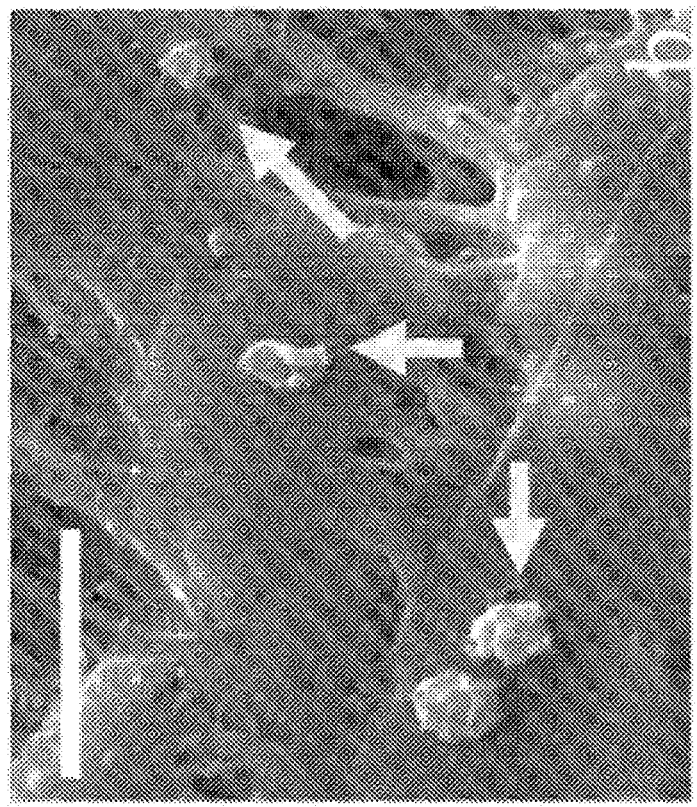
FIG. 6 illustrates platelet adhesion on a) ePTFE and b) POC-ePTFE. Scale bar=10 μm.
Figure 6:
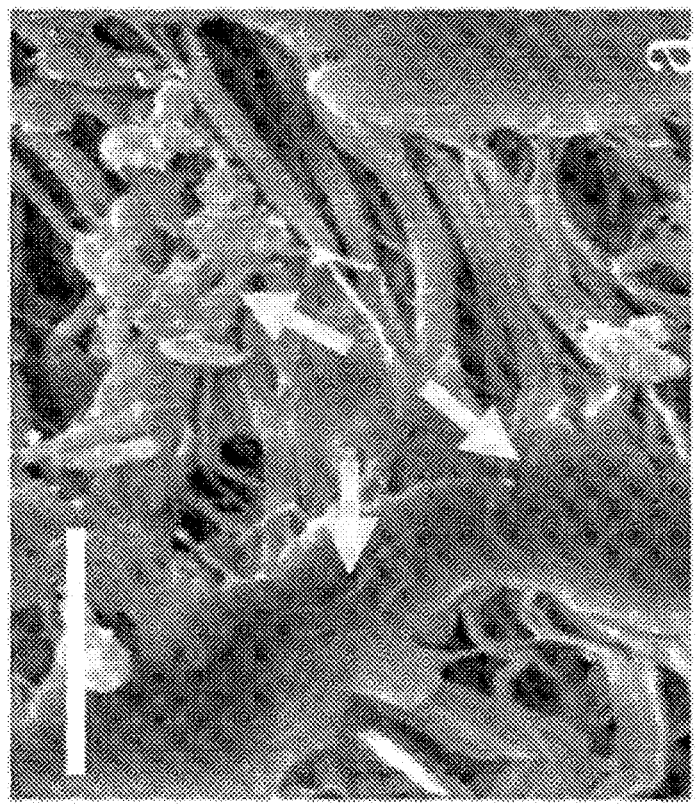

The biocompatibility of POC was assessed in the vasculature in vitro and in vivo, and these results have been published [60, 61]. First, the ability of primary human aortic endothelial cells (HAEC) to adhere and proliferate onto an inert surface, ePTFE, that was coated with POC was assessed. HAEC were seeded onto POC-coated ePTFE and control ePTFE samples and processed for scanning electron microscope (SEM). HAEC attached in significant numbers to the POC-ePTFE samples and not to ePTFE, demonstrating that POC supports endothelial cell growth and attachment (FIG. 5). The degree of platelet adhesion to POC-coated ePTFE was assessed using a modified lactate dehydrogenase (LDH) assay, described by Tamada et al. [62]. A glass surface was used as a positive control for platelet adhesion, spreading and aggregation. There were significantly fewer platelets attached to POC-ePTFE compared to ePTFE, suggesting reduced thrombogenicity (not shown). Platelets that attached to ePTFE formed aggregates and flattened out on the node surface, suggesting platelet activation (FIG. 6). In contrast, the platelets that attached to the POC-ePTFE surface tended to be isolated, had fewer pseudopodia-like extensions, and were rounded in morphology.

Figure 7:
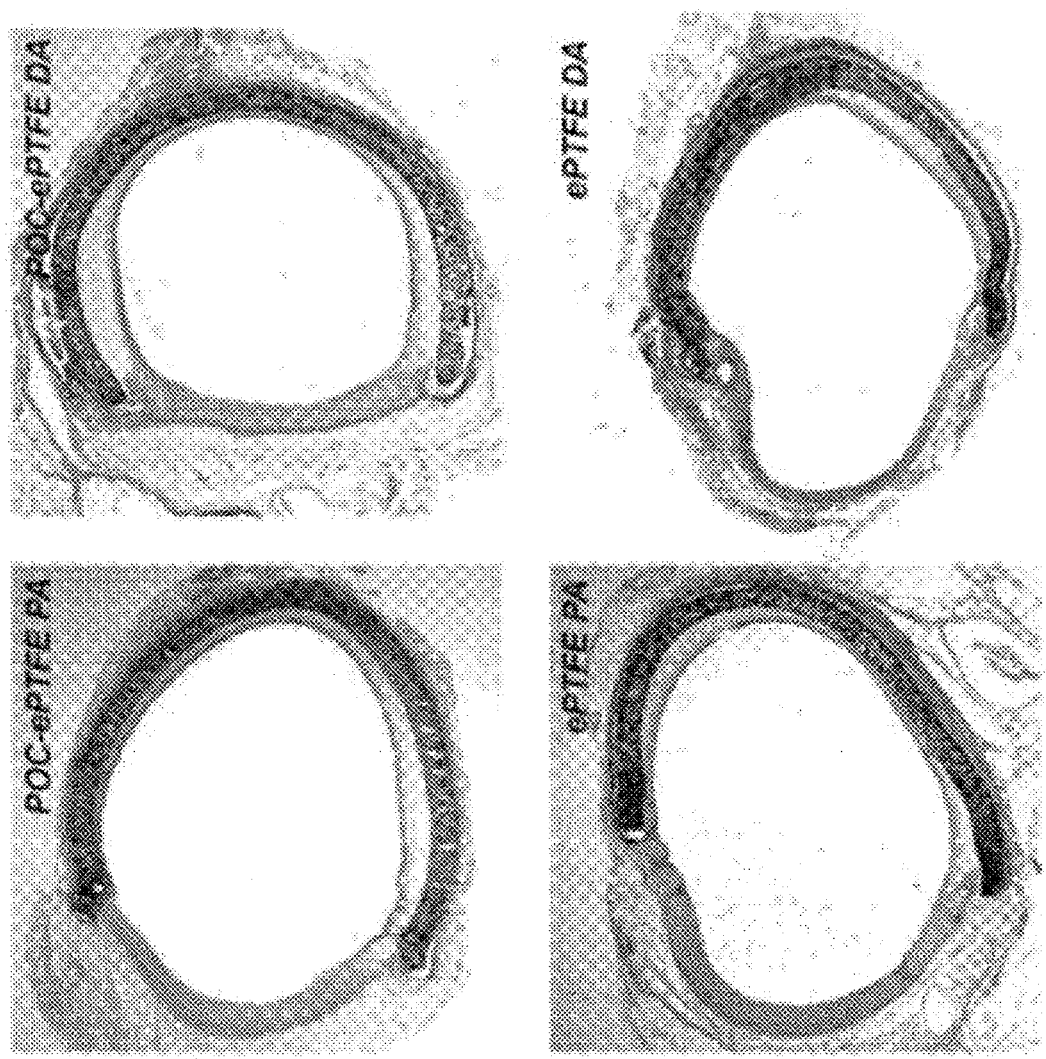
FIG. 7 illustrates that POC-ePTFE grafts resulted in similar neointimal hyperplasia compared to control ePTFE.
Figure 8:
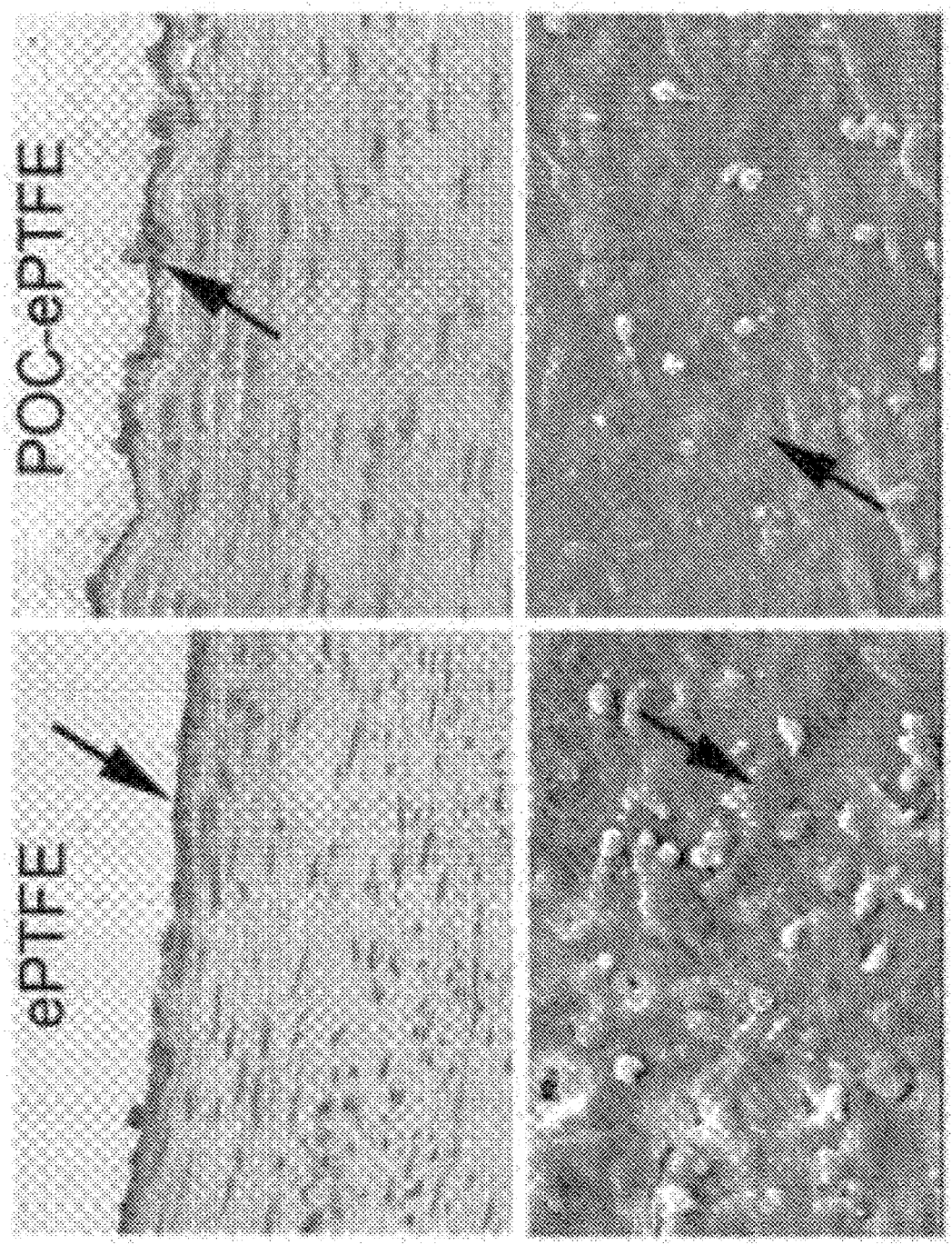
FIG. 8 illustrates that POC supports growth of endothelial cells (brown, arrows) following ePTFE bypass grafting (upper panels). SEM showing endothelial cells (arrows, lower panels).

The biocompatibility of POC in the vasculature in vivo was assessed by coating ePTFE grafts and implanting the POC-ePTFE grafts in the porcine carotid artery bypass model [60]. ePTFE and POC-ePTFE grafts were implanted onto the right and left common carotid arteries and harvested at 7 and 28 days. At 7 days, less macrophage infiltration was observed with the POC-ePTFE grafts (not shown). At 28 days, all POC-ePTFE grafts were patent by magnetic resonance angiography and duplex ultrasonography (not shown), and exhibited statistically similar degrees of neointimal hyperplasia, demonstrating that POC is biocompatible in the vasculature (FIG. 7). An additional benefit of POC is that it supports endothelialization in vivo (FIG. 8). Upon evaluation using immunohistochemical staining for von Willibrand factor, a similar degree of endothelialization throughout the grafts between POC-ePTFE and control ePTFE grafts was observed. This is contrary to the current FDA-approved polymers used to coat the Cypher (Cordis) and Taxus (Boston Scientific) drug-eluting coronary stents, in which endothelialization is inhibited. This represents an additional benefit of the POC as a biomaterial for the vasculature. These results have been submitted for publication.

Development and Assessment of NO-Releasing POC.

Figure 9:
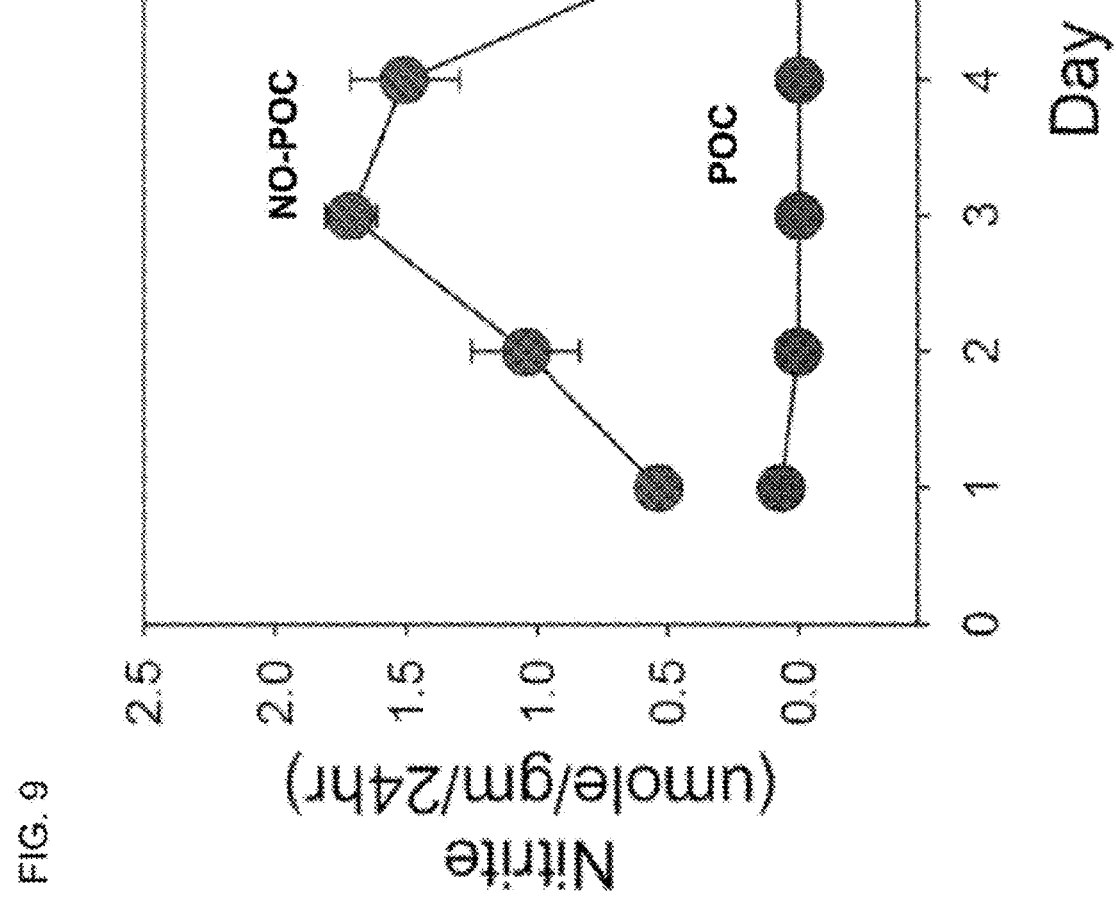
FIG. 9 illustrates nitrite release of control and NO-POC discs.

Having demonstrated the biocompatibility and beneficial properties of POC, the first steps toward fabricating a first-generation NO-releasing POC were completed. A NO-releasing POC was generated by covalently attaching a functional NONOate group to the POC through thermal cross-linking of citric acid, 1,8-octanediol, and an amine diol-based pre-polymer, followed by exposure of the material to gaseous NO for 3 days. Following exposure to gaseous NO, NO-releasing POC discs were evaluated in vitro for nitrite release, an indirect measure of NO release, over time. The NO-POC discs released NO for 7 days compared to controls (FIG. 9). By washing the polymer to leach the nonreactive monomers, the total yield of diazeniumdiolation was increased to 112 µmol/gm NO (FIG. 10), thereby increasing total NO release ~20-fold. These studies are proposed to be further investigated as discussed below.

Formation of POC Stents from Liquid Phase.

Figure 11:
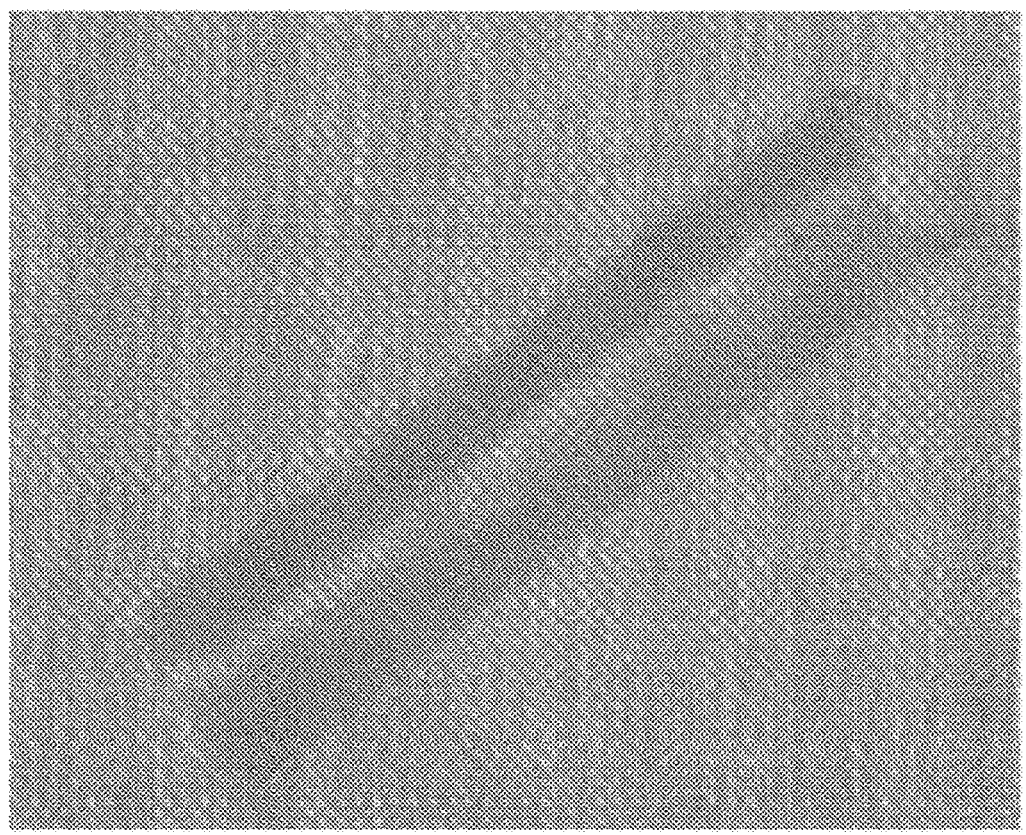
FIG. 11 illustrates the POC scaffold.
Figure 12:
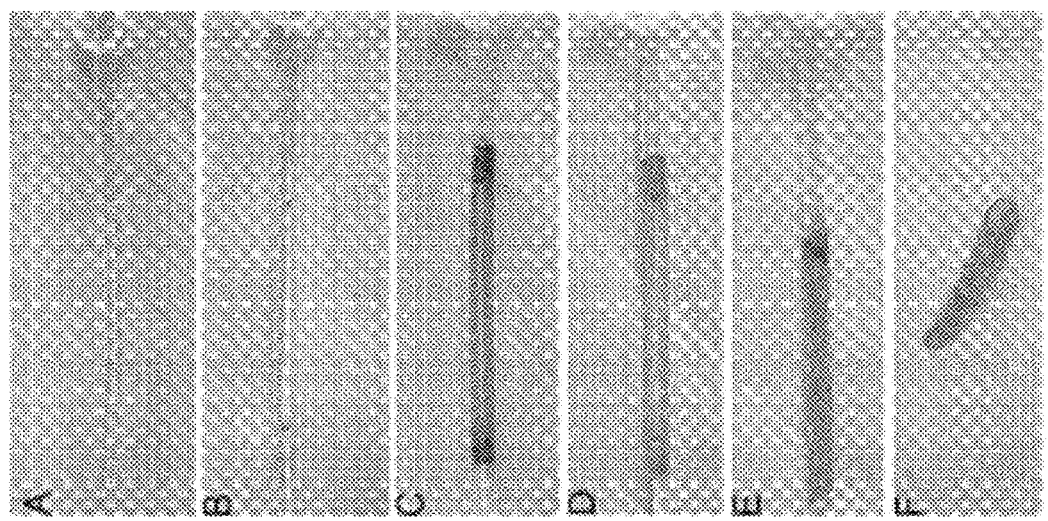
FIG. 12 illustrates that POC forms a stent from liquid phase. A) 3 mm tubing; B) insertion of catheter into tubing; C) injection of POC into tubing; D) polymerization of POC using UV light; E) removal of catheter; and F) Removal of POC cast from the silicone tube revealing a cylindrical stent.

To demonstrate the feasibility of forming a solid stein from liquid, POC was polymerized into cylindrical structures ex vivo in less than 5 minutes at 40° C. (FIG. 11). Furthermore, FIG. 12 demonstrates the injection of the liquid NO-releasing POC material (50 wt % in water) into 3 mm silicone tubing (simulating an artery), followed by inflation of a 3 mm angioplasty balloon to cast the stent, then polymerization of the stent using UV-VIS (~400 nm) light. FIG. 12F shows the material shaped into the form of a cylindrical stent once the silicone tubing was excised, demonstrating that the NO-releasing material maintains elastic recoil after removal of the tubing. Blue dye was added to the POC liquid pre-polymer to aid in the visualization of this process.

Figure 13:
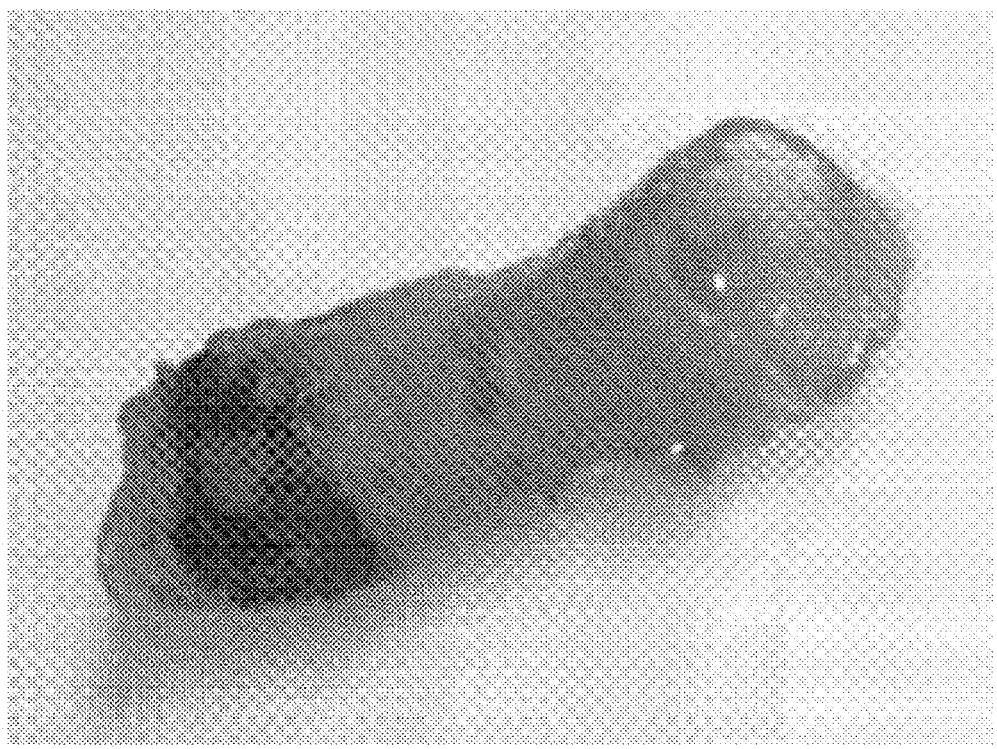
FIG. 13 illustrates a picture of a POC-coated artery after polymerization via UV light.

The inner surface of a harvested porcine artery also was shown to be adherent to a coating comprising NO-releasing POC in order to form a stein from liquid material ex vivo. FIG. 13 confirms the ability of the polymer (dark colored) to adhere to the inner wall of the artery, thereby, increasing its resistance to deformation. These studies are proposed to be further investigated as discussed below.

Development of NO-POC.

Figure 10:
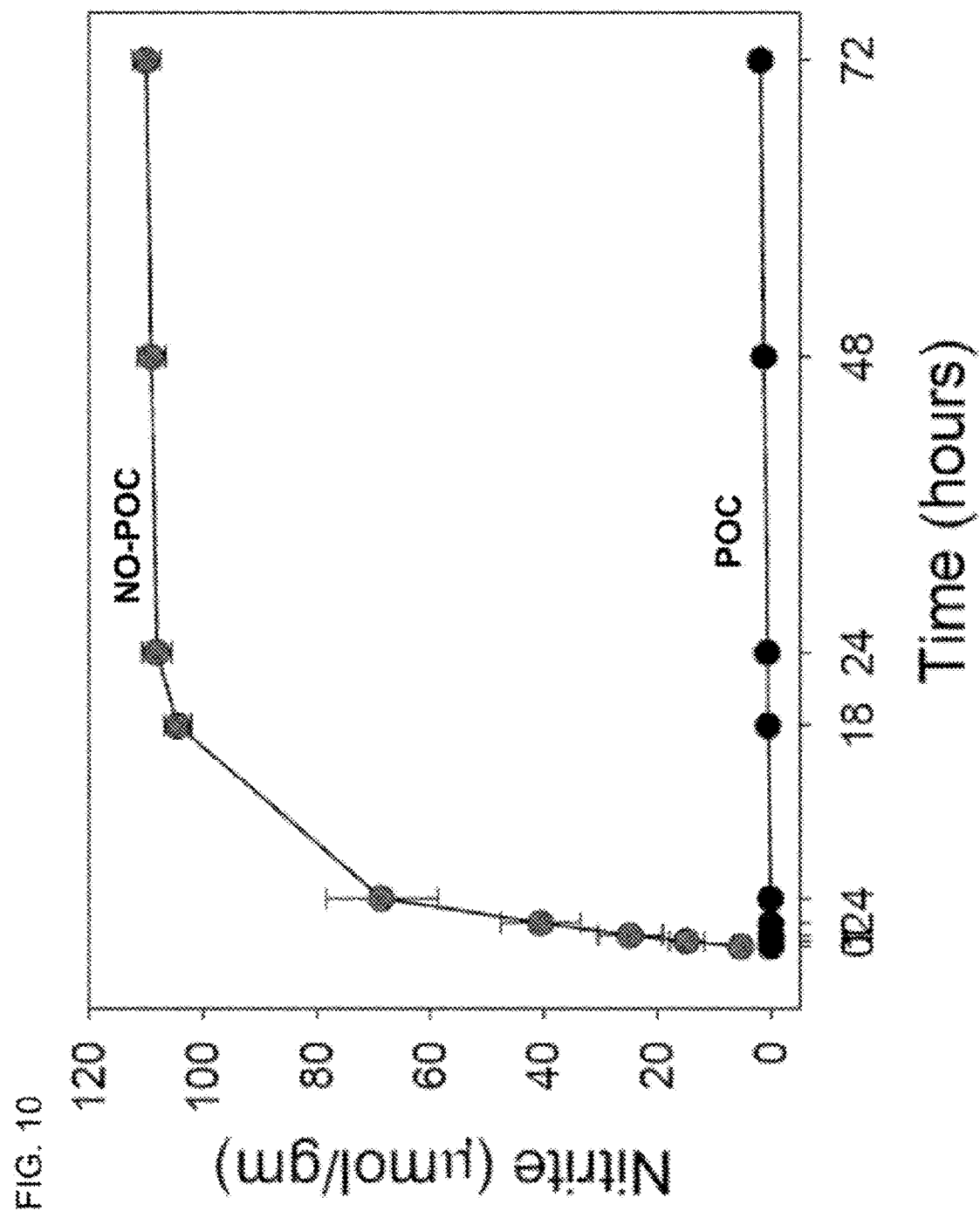
FIG. 10 illustrates cumulative nitrite release after leaching the non-reactive monomers.
Figure 14:
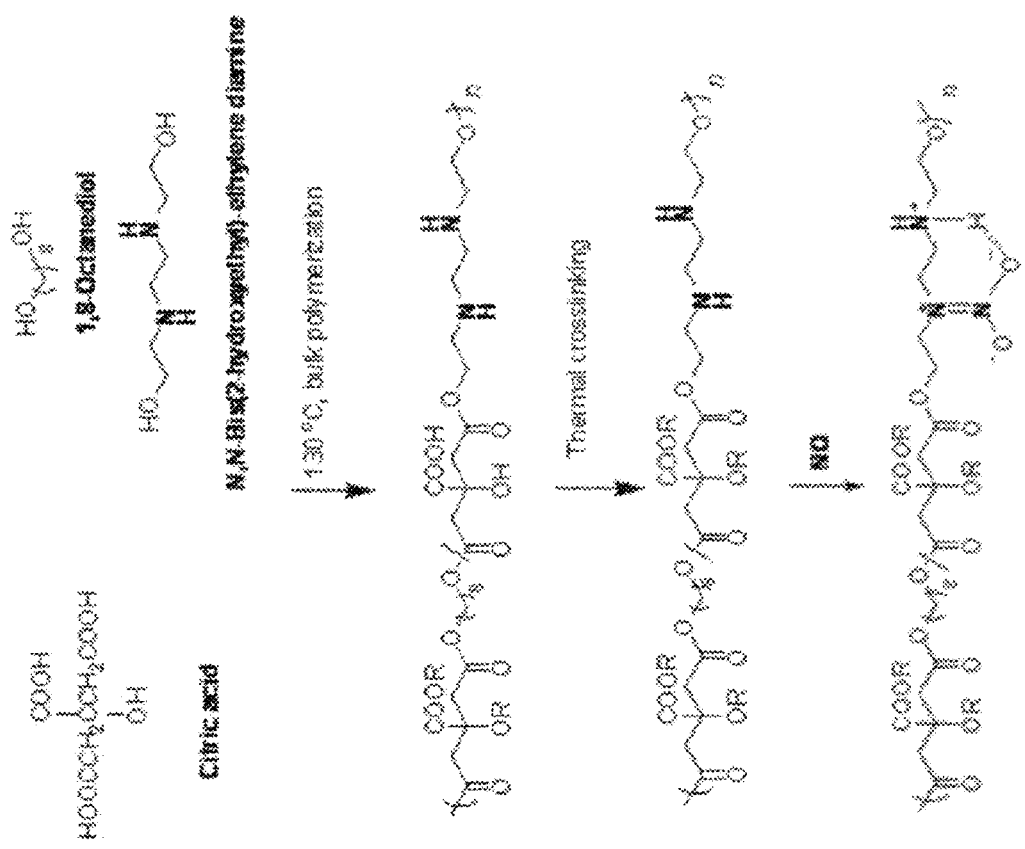
FIG. 14 illustrates the preparation of a biodegradable polymer prepared by cross-linking a prepolymer prepared from a mixture of citric acid, 1,8-octanediol, and N,N-Bis (2-dihydroxyethyl)-ethylene-diamine.

To develop diazeniumdiolated POC (or NO-releasing POC), a functional NONOate group was attached to the POC obtained by thermal cross-linking of a citric acid, 1,8-octanediol, and amine diol-based pre-polymer, followed by exposure of the material, to gaseous NO for 3 days (FIG. 14). From the initial formulation (FIG. 9), NO release was observed for up to 7 days. After leaching out the nonreactive monomers, an approximately 20-fold greater release of NO was observed, mostly within the first 24 hours (FIG. 10). In order to optimize NO release to maintain a sufficient amount of NO for a desired length of time, the number of hydrophobic diols may be increased within the polymer.

Amount and Duration of NO.

To date, it remains unknown how much NO is required in the vasculature to inhibit the subsequent neointimal hyperplasia from developing in humans. In order to estimate how much NO is required in the vasculature to inhibit the subsequent neointimal hyperplasia from developing in humans, the observed NO release may be compared to: 1) data from animal experiments, and 2) known endogenous NO production in humans. The efficacy of the diazeniumdiolate, PROLI/NO, at inhibiting neointimal hyperplasia in rodents was evaluated in vivo and was found to exhibit 91% inhibition when 20 mg was applied periadventitially [39]. Because diazeniumdiolates release 2 moles of NO per mole of compound upon reaction with hydrogen ions, it follows that 20 mg of PROLI/NO releases 160 μmoles of NO. Thus, the current formulation that releases 112 μmole/gm (FIG. 10) is similar to what has been used in rat models. An alternative method of estimating whether the current NO-releasing material will produce sufficient NO is to compare the material against known rates of endogenous NO release. Vaughn et al. reported that resting endothelial cells in the vasculature constitutively release ~4 pmol/min/mm$^2$, which equals 5.8 nmol/24 hr/mm$^2$ [19]. From preliminary data, the presently disclosed films can produce 112 μmole/gm/24 hr. The surface density of these films is on the order of ~0.0003 gm/mm$^2$. Hence, these films can generate 34 nmol/24 hr/mm$^2$. This value is approximately 6 times that of endogenous NO production from endothelial cells. Given that iNOS produces ~100-fold more NO than eNOS, this level of NO production in the vasculature is not expected to be toxic to the surrounding tissue. Thus, whether calculating NO required according to small animal surgery results, or by calculations according to surface area and known endogenous NO release, the NO release from the presently disclosed material should be sufficient and effective to result in a biological effect and not be toxic. Furthermore, modifications that will increase the amount and duration of NO production will remain within physiologically relevant and safe values.

Also of interest is how much NO will reach the tissue from the NO-releasing POC. NO release will occur at the blood-polymer interface, throughout the polymer, and at the polymer-tissue interface upon reaction with hydrogen ions in the circulating blood or tissue. Because NO is a highly diffusible molecule, NO is expected to have a biological effect on the underlying tissue, in addition to being quenched by circulating hemoglobin. Demonstrating the feasibility of this stent-based approach, Fishbein et al. fabricated NO-releasing stainless steel stents [41]. These NO-releasing metallic stent inhibited neointimal hyperplasia by 50% in a rat model. Alternatively, demonstrating the diffusible nature of NO, when applied to the periadventitial surface of the artery, NO very effectively inhibits neointimal hyperplasia and accelerates re-endotheilialization [39, 40]. Thus, while not directly demonstrated, it can be inferred from these data that NO is diffusing through the wall of the artery to effect the endothelial cell layer, in addition to the adventitial fibroblasts and smooth muscle cells.

The disclosed NO-POC material has been observed to release approximately 6-fold greater NO than endogenous NO release. The duration of NO release may be increased by increasing the number of hydrophobic diols in the POC. The amount and duration of NO release from the modified POC material will then quantified by analyzing nitrite release, an indirect measure of NO production, as well as measuring total NO release using the Apollo 4000™ Nitric Oxide Analyzer (World Precision Instruments). Ideally, the modified material will release NO with a half-life of approximately 7 days, given the kinetics of vascular healing. Optionally, the amount of NO release may be increased further by increasing the number of functional NONOate groups that are attached to the POC backbone via increasing the amine diol content. Also, optionally, the length of time the modified material is exposed to gaseous NO may be increased. Finally, optionally, the duration of NO release may be increased further by increasing the pH of the modified material, as diazeniumdiolates release NO more slowly under basic conditions.

The volume of pre-polymer that is required to coat the artery should be reasonable within a confined space provided by a delivery catheter. With respect to the volume of the NO-POC pre-polymer that will be delivered to the artery, an artery that is 5 mm in diameter by 6 cm in length (surface area=942 mm$^2$) would require approximately 0.3 gm of polymer for coating. This mass represents the injection of a pre-polymer solution volume of ~0.6 ml at 50 wt % pre-polymer concentration.

Bioactivity of NO-POC.

After NO release is assessed and optimized, the biological effect of this material will be evaluated in vitro by exposing it to blood under both static and flow conditions and determine platelet adherence with scanning electron microscopy and lactate dehydrogenase release. An ex vivo perfusion circuit in which both flow and pressure can be modified has been described [61]. In order to form the solid material that will be used for the stent, the POC pre-polymer may be acrylated via the hydroxyl group to allow for radical-initiated thermal or photo polymerization.

Next, the interaction of both endothelial cells and VSMC with the NO-releasing POC material will be evaluated. For the endothelial cells, the ability of endothelial cells to adhere and grow on tissue culture wells coated with the NO-releasing POC will be assessed. Attachment of endothelial cells will be assessed using a parallel plate flow chamber using defined shear stresses (5-20 dynes per square centimeter). Proliferation of endothelial cells to the NO-releasing POC will be assessed with tritiated ($^3$H) thymidine incorporation. For the VSMC, proliferation will be assessed by coating tissue culture wells with the NO-releasing POC and measure $^3$H thymidine incorporation in VSMC plated in the wells. For all of the experiments above, appropriate controls will be assessed, which will consist of POC material that does not release NO, and wells not coated with any POC. The effect of endothelial cells and VSMC on proliferation against that observed with standard diazeniumdiolate donors also will be assessed. Given that diazeniumdiolate donors can and have been created with a wide range of half-lives, a donor with a half-life that is appropriate for the assay being conducted will be assessed. For example, DETA/NO has a half-life of 20 hours. This would be appropriate for proliferation studies in which the time point is 24 hours.

Preliminary data suggests that a NO-releasing POC can be prepared that will release at least 5-fold greater NO compared to endogenous NO production with a half-life of 7 days. Furthermore, preliminary data suggest that the NO-releasing POC will support endothelial cell attachment and growth, inhibit platelet adherence, and inhibit VSMC proliferation in vitro to a much greater extent compared to non-modified POC.

Ideally, the biodegradable stents described herein release sufficient NO for 7 days in order to inhibit both thrombosis and neointimal hyperplasia, yet stimulate endothelial cell proliferation in vivo. As disclosed herein, the desired amount and duration of NO release may be assessed and modulated. Studies of arterial injury have demonstrated that complete endothelialization occurs between 7-14 days following arterial injury. As such, a stent that will release NO with a similar half-life may be desirable. In addition to modifying the number of functional NONOate groups attached to the POC and ensuring maximal loading of NO by varying the length of time the material is exposed to gaseous NO, other modifications may be required. For example, time-release microspheres that have different degradation profiles may be included in the prepolymer solution. Or, diazeniumdiolate pro-drugs may be administered to extend NO release.

Polymerization.

In order to form a solid stent from liquid, polymerization conditions to polymerize the liquid NO-releasing POC material in the least amount of time should be optimized. For example, after administering the prepolymer solution to the site of stent formation, polymerization or cross-linking may be initiated by introducing a radical initiator to the prepolymer solution. Other investigators have demonstrated the efficacy and safety of in situ radical polymerization of tissue [63-66]. Optionally, polymerization or cross-linking may be initiated or enhanced by heating the prepolymer solution at the site of stent formation. Intravascular devices currently used in patients result in changes to the intravascular temperature. The Rotablator rotational atherectomy device was found to result in temperature increases of 2-4° C. with minimal decelerations but increases of 11-14° C. with continuous ablation or rapid decelerations [67]. The Boston Scientific Cryoplasty Therapy freezes tissue to −10° C. Both of these later devices are FDA approved and are well-tolerated by the surrounding tissue. Optionally, polymerization or cross-linking may be initiated or enhanced by subjecting the prepolymer to light (e.g., UV light) at the site of stent formation. With respect to UV light polymerization, UV light is commonly used to treat a variety of skin pathologies in patients. Thus, damage to the surrounding tissue from either thermal or photo-initiated polymerization is not expected, as the temperatures are in alignment with what is currently used, the polymerization is highly localized to the interface of the vessel, and excess or non-reacted monomers will be aspirated out of the reaction volume. If temperature is used to begin the radical polymerization reaction, initiators that are efficiently activated at 40° C. are commonly available. If UV-VIS (365 nm) is used, a fiber-optic probe can be inserted within the delivery catheter. In both cases, the results disclosed herein demonstrate that the reaction can be completed within 5 minutes.

In future work, experiments are proposed: 1) to optimize the conditions for polymerization within 1-2 minutes; and 2) to evaluate and optimize the mechanical characteristics of the polymerized stent for the vasculature. For this aim, w both thermal- and photo-initiated methods to induce polymerization will be evaluated in order to determine the most optimal method for in vivo applications as well as measure and optimize the mechanical properties of the stented artery. As shown herein, POC can be formed into cylindrical bioengineered vascular grafts [68]. These bioengineered grafts were implanted into pigs using the carotid artery bypass model for 7 days and were found to be durable and biocompatible (not shown). Thus, this experiment suggests that POC has characteristics suitable for the vasculature, including sufficient strength to withstand arterial pressure and pulsatility. Different methodologies to induce polymerization of POC into cylindrical casts in situ using both mild heat (~40 C) and UV light will be evaluated. Preliminary data suggest that acrylated POC can be polymerized in a short period of time using UV-VIS light (FIGS. 12-13) or temperatures as low as 40° C. (FIG. 11), which should be compatible with in vivo applications. Thus, the POC prepolymer will be acrylated via the hydroxyl group to allow for radical-initiated thermal or photo polymerization. Various conditions will be modulated to maximize polymerization including degree of acrylation, prepolymer molecular weight, polymer solubility, and polymer viscosity. Parameters that will be assessed include: 1) time to polymerization, 2) polymer tensile strength, 3) polymer elasticity, 4) polymer compliance, and 5) biocompatibility with endothelial cells and VSMC (i.e., effect on apoptosis, migration, and proliferation). Ideally, polymerization will be completed within 1-2 minutes with one of these two approaches, as these times are well suited for clinical applications in patients based on the time required to use other devices commonly in use for treating atherosclerosis.

Polymer Solubility.

With respect to the solubility of the prepolymer, water-soluble polydiol citrates may be synthesized by using poly (ethylene glycol) and glycerol diacrylate as the diol monomers. However, the use of ethanol/water solutions as a solvent for the pre-polymer also is possible and offers a broader range of pre-polymers (e.g., using as solvent 50:50 ethanol:water). The contact time between the solvent and the "damaged" blood vessel is minimal and the ethanol:water solution would not be expected to cause any major long-standing damage to the artery. However, stent formation will be tested using water or water:ethanol as a solvent for the prepolymer solution for forming the stent. Parameters that will be assessed are the same as described above.

Polymer Viscosity.

The viscosity of the prepolymer is on the order of 100 centipose (cp) and a 30 wt % dilution has a viscosity of approximately 10 cp. If needed, the viscosity of the liquid phase can be adjusted with the volume of saline that is used to dissolve the pre-polymer. Initially, a 30 wt % prepolymer solution will be tested.

Stent Formation.

Stents will be cast in freshly harvested porcine arteries ex vivo under static conditions, similar to what was shown in FIG. 13, discussed above. Stents will be cast using ideal polymerization conditions as determined herein. Fresh porcine arteries will be obtained from the local slaughter house (Park Packing Company, Chicago, Ill.). After injection of the NO-POC into the lumen of the artery, the stent will be polymerized with the use of a 4-6 mm angioplasty balloon (to be determined by the diameter of the artery that will be used) and either thermal or photo-initiation, based on the experiments described herein. A thermal radical initiator that is efficiently activated at 40° C. may be utilized. Initiator amounts will be kept to less than 1% of the prepolymer content. The pre-polymer content (in an aqueous solution) typically is about 30 wt %. If photo-initiation will be used, UV-VIS having a wavelength of 365 nm will be utilized. Parameters that will be assessed include: 1) time to complete polymerization, 2) % non-reacted monomers retrieved, 3) % surface area coated, 4) thickness and homogeneity of the stent coating, and 5) attachment strength to the surrounding tissue. Lastly, once the polymer has been formed within the walls of the blood vessel it will be important for the elastomeric and adhesive properties to remain intact to prevent fragmentation and potential loss to the blood stream. As the polymer is a cross-linked network with elastic properties fragments are not expected to form. However, this will be measured as described below. Ideally, 100% surface area coverage in a homogeneous manner will be achieved with less than 10% of monomers being un-reacted and retrieved.

Evaluation of Stent Mechanical Properties.

After determining the ideal conditions for liquid cast stent polymerization, the physical and mechanical characteristics of the stent will be measured and compared to those characteristics of healthy arteries and to those of commercially available balloon expandable and self-expanding metallic stents.

Radial strength measures the resisting force in Newton (N) of the stent when a strain of 0.5 is applied in the radial direction (i.e., a diameter reduction of 50%). Current metal self-expanding stents on the market have radial strength of 2-4 N against a strain of 0.5, while metal balloon expanding stems have radial strength of 5-6 N [69]. Radial strength may be measured using a range of different strains, from 10 to 100% diameter reduction.

Axial strength measures the resisting forces in Newton of the stent when a strain is applied in the axial direction. This will be measured using forces that result in up to 50% axial deformation. Thirty percent (30%) axial deformation is the greatest axial deformation that has been shown in the superficial femoral and popliteal arteries [70].

Elastic deformation refers to changes in shape that disappear completely after release of external forces. When external forces exceed the limit of elastic deformation, stents become deformed or fractured, resulting in a permanent change in shape. Thus, the tolerance of the stent to deformation forces ranging from 10 to 100% will be measure. Balloon expandable stents do not tolerate deformation forces greater than 10% [71]. Self expanding metallic stents tolerate much greater deformation forces. Preferably, the stent prepared as described herein tolerates a deformation force of at least 80%.

Flexibility (or conversely stiffness) measures the resistance of the stent to bending. Current stents on the market vary considerably with this parameter, ranging from $0.5 \times 10^{-2}$ to $150 \times 10^{-2}$ N per 10 degree flexion [69]. The higher the force, the less flexible the stent.

Compressive strength and modulus will be measured using the Instron mechanical tester. Compressive strength equals the compressive force per unit area the material can withstand. Compressive modulus (or Young's modulus) equals change in stress divided by change in strain. Compression will be exerted in 0.2-mm increments. Young's modulus will be measured. Preferably, the stent prepared as described herein has a compression strength and modulus within 10% of commercially available self-expanding stents.

Propensity to fracture will be measured by deploying a stent in a silicone tube and exposing the stent to repetitive bending, which will be performed using a specially designed bend fatigue test machine. After the stem is deployed, saline will be circulated through the closed circuit tubing. The fatigue tester will be set to cycle at 7 Hertz for 10 million cycles. The stent will be visually inspected for fractures every 24 hours until completion. Commercially available self-expanding metallic stems may be tested for comparison. Under these conditions, Nikanorov et al. reported stem fracture rates ranging from 0-80% when they evaluated 6 commercially available self-expanding metallic stems. Preferably, the stent prepared as described herein has a 0% fracture rate (or a fracture rate less than 1% or 2%), which will be similar to both the S.M.A.R.T. Control stem (Cordis/J&J) and the Protégé EverFlex stent (EV3).

Although the stents described herein may be compared to commercially available self-expanding metallic stents, it is possible that a biodegradable polymeric stent may require different mechanical characteristics to produce a similar favorable outcomes following in vivo deployment. In future studies, the stem described herein will be deployed in vivo and subjected to physiologic forces and conditions and evaluated for durability and efficacy Biocompatibility.

With respect to the biocompatibility of the pre-polymer, it is expected to be adequate as the monomer components are non-toxic. Furthermore, extensive biocompatibility studies in the pig with POC-coated ePTFE grafts have been performed and POC has been found to be very biocompatible (See Results described herein). However, the biocompatibility of the pre-polymer will be further assessed as it contacts the vasculature wall. Upon polymer degradation, water soluble oligomers of glycerol/polyethylene glycol/citric acid would be slowly released to the surrounding tissue and the blood stream. These monomers are nontoxic compounds that are normally excreted by the kidney. The biocompatibility of these monomers will be evaluated by exposing them to freshly harvested porcine arteries for increasing lengths of time (1 hour-5 days) using an ex vivo organ culture system [72]. Parameters that will be assessed include: 1) histologic evidence of cell death through either apoptosis or necrosis, 2) loss of cellular architecture via (H&E staining), and 3) alternation in the structural aspects of the arterial wall (using Mason's trichrome and/or Verhoeff von Gieson staining).

Ideally, the liquid cast biodegradable stent disclosed herein comprises NO-releasing POC and is cast using mild heat or light in less than about 10 minutes (preferably less than about 5 minutes, more preferably less than about 2 minutes (e.g., 1-2 minutes)). Furthermore, ideally the stent demonstrates characteristics that are favorable for an arterial environment, such as adequate surface area coverage, thickness homogeneity, tissue ingrowth, radial and axial strength, elastic deformation, flexibility, compressive strength, and low propensity to fracture, as defined above. Conditions that may be varied in order to modulate polymerization time or characteristics of the stent include increasing the number of acrylated POC in the prepolymer solution in order to increase cross-density of the polymerized stent. Other options will be to use a shorter diol to increase the cross-link density. In addition to modifying the strength of the polymer by varying the amount of the acrylated monomer, the thickness of the polymer coating on the vessel wall also may be varied. This parameter will be determined by the atmospheres of inflation used to cast the balloon.

Catheter Development.

In order to deliver the liquid prepolymer to the intravascular space and polymerize it into a solid, a specialty catheter is required that can do the following: 1) occlude flow at the desired target site, 2) deliver the liquid prepolymer, 3) be able to initiate polymerization, 4) be able to cast the polymer into a cylindrical stent shape with desired thickness and no edge effect, and 5) be able to aspirate non-reacted monomers. A proposed catheter for delivering the prepolymer is described in U.S. Provisional Patent Application No. 61/323,953, filed on Apr. 14, 2010 and a U.S. Utility Application filed concurrently herewith and entitled "Triple Balloon Occlusion Catheter," (inventor Melina R. Kibbe, serial number of the application yet to be assigned).

Evaluation of the Liquid Cast Stent System in an Ex Vivo Perfusion Circuit.

A working prototype of the above-described catheter will be utilized to deliver and test the liquid cast stent in an ex vivo perfusion circuit and in freshly harvested porcine arteries. These experiments will provide data related to performance of the delivery catheter as well as the ability to polymerize a stent from liquid under conditions of flow, pressure, and pulsatility. For these experiments, normal saline or Lactated Ringer's solution will be utilized as they are physiologic to human blood and are often administered to patients. This perfusion circuit has the ability to modify both flow and pressure [73].

Parameters that will be assessed include: 1) time to complete polymerization, 2) % non-reacted monomers retrieved (via HPLC), 3) % surface area coating, 4) thickness of the stent coating (by ultrasonography, gross evaluation, and histology), 5) homogeneity of the stein thickness, 6) edge effect (by gross appearance), 7) turbulence (by ultrasonography), 8) attachment strength to the surrounding tissue, 9) compression strength and modulus, 10) flexibility (or conversely, stiffness; i.e., ability to resist fractures and cracking with external compression), 11) elastic deformation, 12) radial strength, 13) axial strength, 14) propensity to fracture, and 15) distal fragment loss (i.e., fragmentation under flow). These parameters will be measured as described herein. Biocompatibility will be assessed with histology and immunohistochemistry. Distal fragment loss will be evaluated by using a distal filter in the perfusion circuit to capture fragmented debris. The size, mass, and volume of the fragments will be quantified.

Although fragmentation is not expected, if observed, fragmentation can be minimized by modifying the crosslink density of the pre-polymer to obtain a more elastic stent. If the stent is observed to have insufficient attachment strength to the adjacent tissue, peptide sequences for transglutaminase may be added to the pre-polymer in order to crosslink the polymer to the surrounding vessel wall. If the stent does not provide sufficient compression strength to resist elastic recoil, the thickness and crosslink density of the polymer can be modified to accommodate those forces. This modification can be performed by choosing a shorter diol monomer or by increasing the acrylated monomer content.

Cell Culture.

Endothelial cells and VSMC will be isolated and cultured from the abdominal aortas of pigs. VSMC will be harvested according to the collagenase method described by Gunther et al. [74]. Endothelial cells will be harvested using the method described by Mahabeleshwar et al. [75]. VSMC will be maintained as previously published [40]. Endothelial cells will be maintained in media containing DMEM (high glucose) with 25 mM HEPES, 10% FBS, 90 µg/mL heparin sulfate, 90 µg/mL endothelial cell growth factor, 10,000 U/mL penicillin, and 10 mg/mL streptomycin [75].

Proliferation Assay.

Cells will be plated in 12-well plates and growth-arrested for 24 hours, after which they are exposed to in the presence of $^3$H thymidine (5 µCi/ml) for an additional 24 hours. $^3$H-thymidine incorporation into trichloroacetic acid-precipitated DNA are quantified by scintillation counting.

Apoptosis.

Cells will be plated in 12-well plates in media for 24 hours. Growth medium will be collected (to obtain any floating cells), and wells will be rinsed with 1× Hank's Balanced Salt Solution (HBSS) to collect all detached cells. Cells will be harvested by incubation for 5 minutes at 37° C. in trypsin. Collected cells will be centrifuged at 1200 rpm for 5 minutes to pellet live and dead cells, the supernatant removed, and the cells re-suspended in 1×HBSS. Cells will be diluted five-fold in Guava ViaCount Reagent and cell death assessed by Guava PCA.

Ex Vivo Perfusion Circuit.

A recirculation system has been set up to perfuse vascular grafts [76]. This set up may incorporate and artery and simulate the stenting procedure. The circuit can accommodate flow rates of up to 700 ml/min and pressures in the range of 60 to 200 mmHg. Pulsatile flow can also be adjusted as described previously [73]. The perfusion circuit can be adapted to the compliance measurement device if necessary.

Tissue Processing and Routine Histology.

Harvested and stented porcine arteries will be fixed in formalin overnight. The samples will be cut into 5 mm sections embedded in paraffin. 5 µm sections will be cut throughout the entire stented segment. Sections will undergo routine hematoxylin-eosin staining. To evaluate elastin and collagen, the modified Verhoeff von Gieson and Massons trichrome stains will be used.

Apoptosis (in Tissue).

Apoptosis will be evaluated in the arteries by terminal deoxynucleotidyl transferase-mediated dUTP-biotin nick-end labeling (TUNEL) using a commercially available system according to manufacturer's instructions.

Platelet Adhesion.

The degree of platelet adhesion to NO-POC coated plates will be assessed using a modified lactate dehydrogenase (LDH) assay, described by Tamada et al. [62]. A glass surface will be used as a positive control for platelet adhesion, spreading and aggregation. SEM may be used to visually quantify platelet adhesion to the NO-POC material.

Physical Properties of the Stent.

Elastic Deformation, Flexibility, Radial Strength, and Axial strength will be measured using instruments known in the art, for example, instruments available from Instron Corp for testing mechanical properties of materials:

The compression strength and modulus of the stents and stented arteries also may be tested with an Instron mechanical tester. This instrument places a downward pressure on the sample and the instrument records the forces as the probe moves downward. Propensity to fracture may be measured using methods in the art, e.g., methods utilized an published by the Northwestern University Mechanical Testing Core Facility.

Regarding adhesion strength, it is expected that contact between the copolymer and the tissue will be such that an interface between the two will not be clearly delineated. Nevertheless, adhesion strength of the polymerized NO-POC layer to the vessel wall will be assessed in vitro by applying a modified peel test using an Instron mechanical tester. The force required to remove the copolymer from the vessel wall will be normalized to the contact surface area.

Statistical Analysis.

For statistical analysis, data will be reported using the mean+/−the standard error of the mean. Differences between more than two groups will be determined using one-way analysis of variance. Statistical significance will be assumed for $P<0.05$. Difference between two groups will be determined using the Student's t-test.

Example 2

Determination of Optimal Polymerization Conditions.

A liquid cast stent was prepared in a silicon tube (simulating an artery) as described in Example 1. (See FIG. 12 and accompanying text). The following polymerization scheme was utilized.

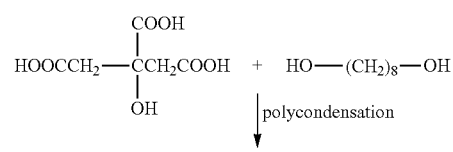

Scheme 1.

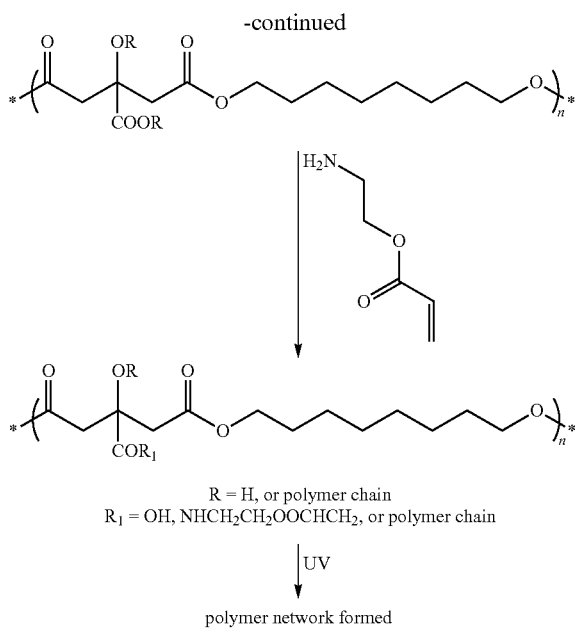

Figure 15:
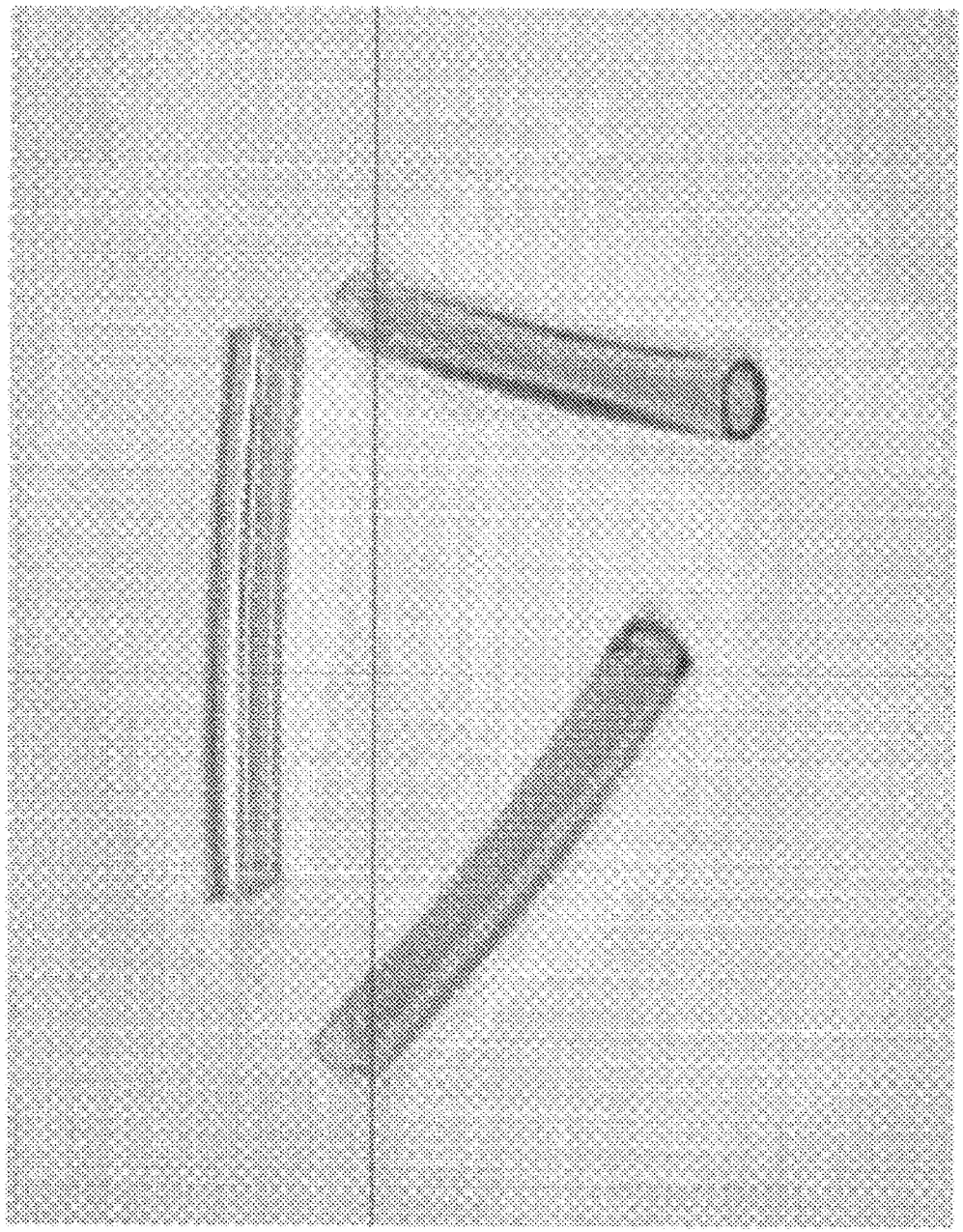
FIG. 15 illustrates stems formed from acrylated POC prepolymers and treated with UV light having a wavelength of 365 nm for 1-2 minutes.

In the scheme, POC is formed by polycondensation and subsequently acrylated with $NH_2CH_2CH_2OOCCHCH_2$ and treated with UV light having a wavelength of 365 nm for 1-2 minutes. Stents thus formed are shown in FIG. 15.

NO Release from Diethyl DETA POC and PDDC Cast Stents.

Figure 16:
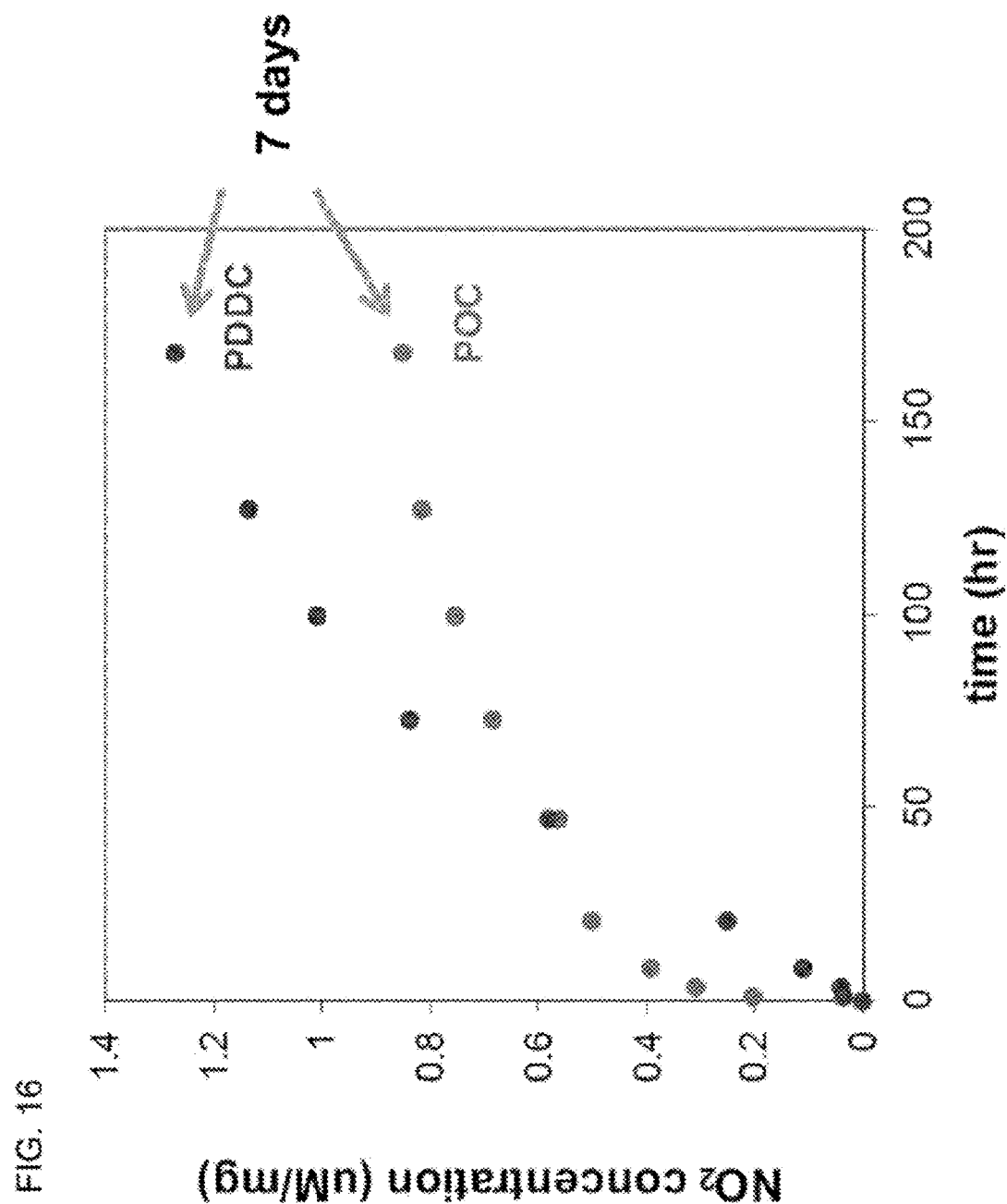
FIG. 16 illustrates NO-release from diethyl DETA POC and PDDC cast stents as measured using a Griess Test in PBS Buffer (pH 7.4, 37° C.).

NO-releasing diethylenetriamine ("DETA") POC and PDDC cast stents were prepared as described in Example 1. NO release was measured using a Griess Test in PBS Buffer (pH 7.4, 37° C.). (See FIG. 16). $NO_2$ concentration was measured and achieved maximum release in as little as 7 days.

Biodegradation Properties.

Figure 17:
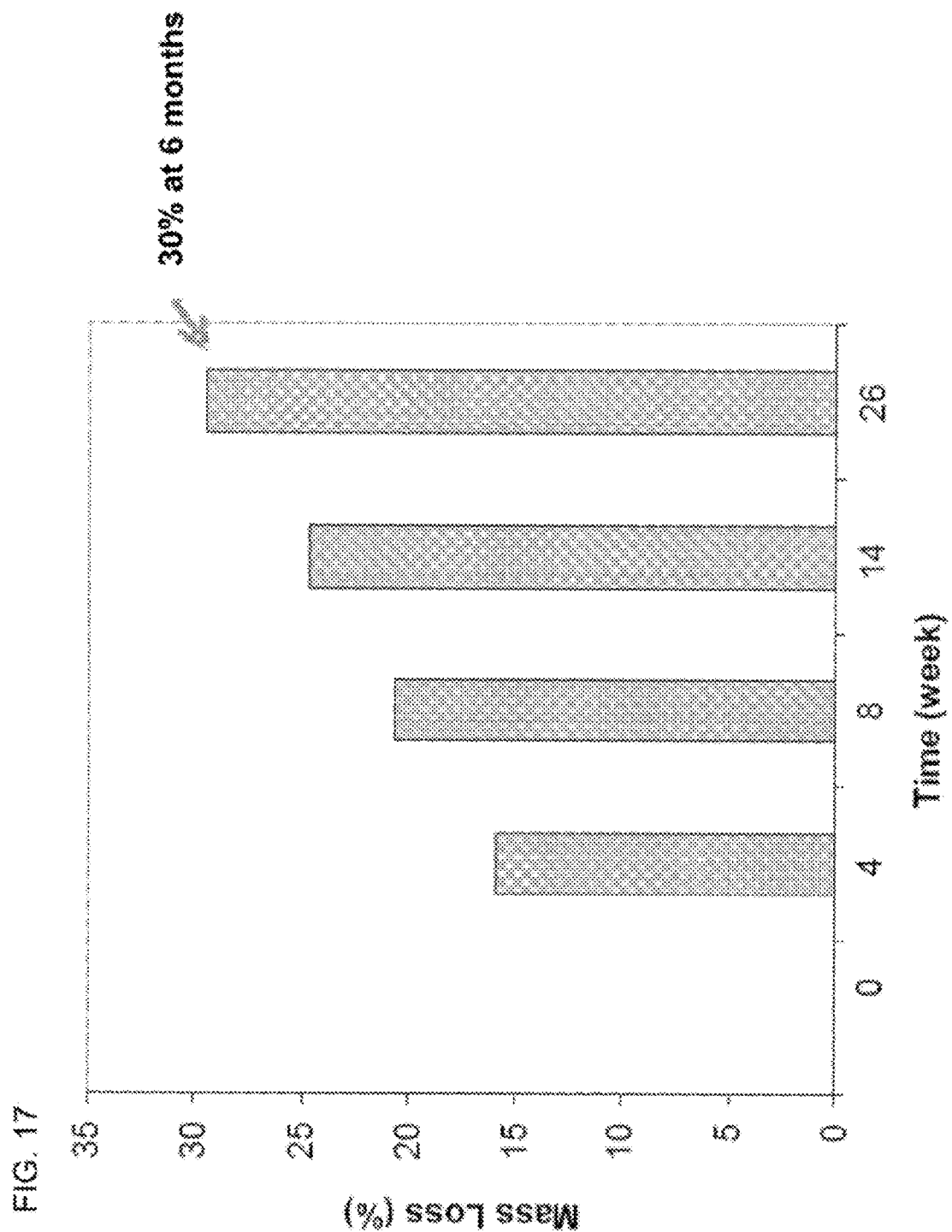
FIG. 17 illustrates biodegradation of photo-crosslinked POC incubated in PBS buffer (pH 7.4, 37° C.).

The biodegradation properties of photo-crosslinked POC were determined. Photo-crosslinked POC prepared as in Example 1 was incubated in PBS buffer (pH 7.4, 37° C.). Periodically, the photo-crosslinked POC was weighed and percentage mass loss was calculated. (See FIG. 17). The photo-crosslinked POC lost 30% of original mass at 6 months.

Mechanical Properties—Tensile Strength.

Figure 18:
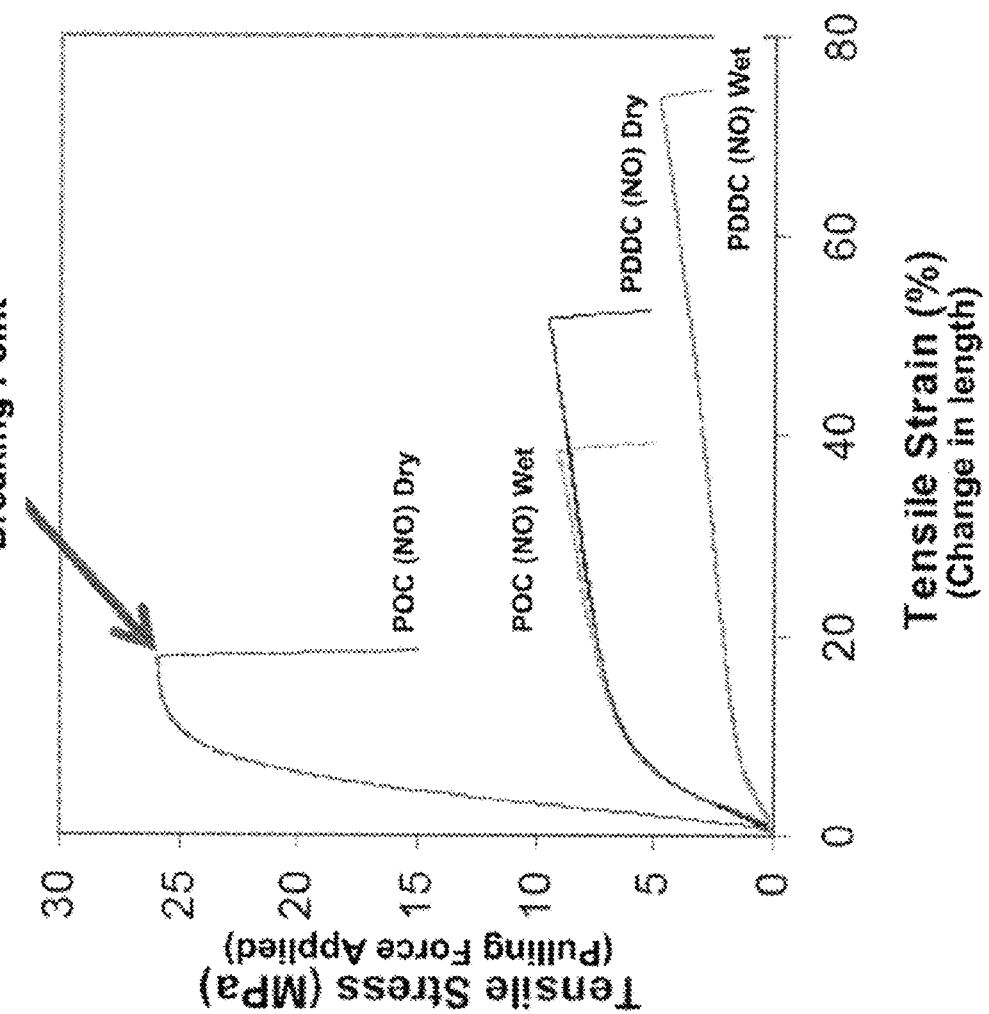
FIG. 18 illustrates a comparison of the tensile strength of a wet stent versus a dry stent comprising either POC (NO) or PDDC (NO) by applying a pulling force (Tensile Stress MPa) and measuring change in length (Tensile Strain (%).

POC (NO) and PDDC (NO) stents were prepared in silicon tubing as described above. The tensile strength of a wet stent versus a dry stent comprising either POC (NO) or PDDC (NO) was compared by applying a pulling force (Tensile Stress MPa) and measuring change in length (Tensile Strain (%)). (See FIG. 18).

Mechanical Properties—Ability to Withstand Deformation via Radial Compression.

Figure 19:
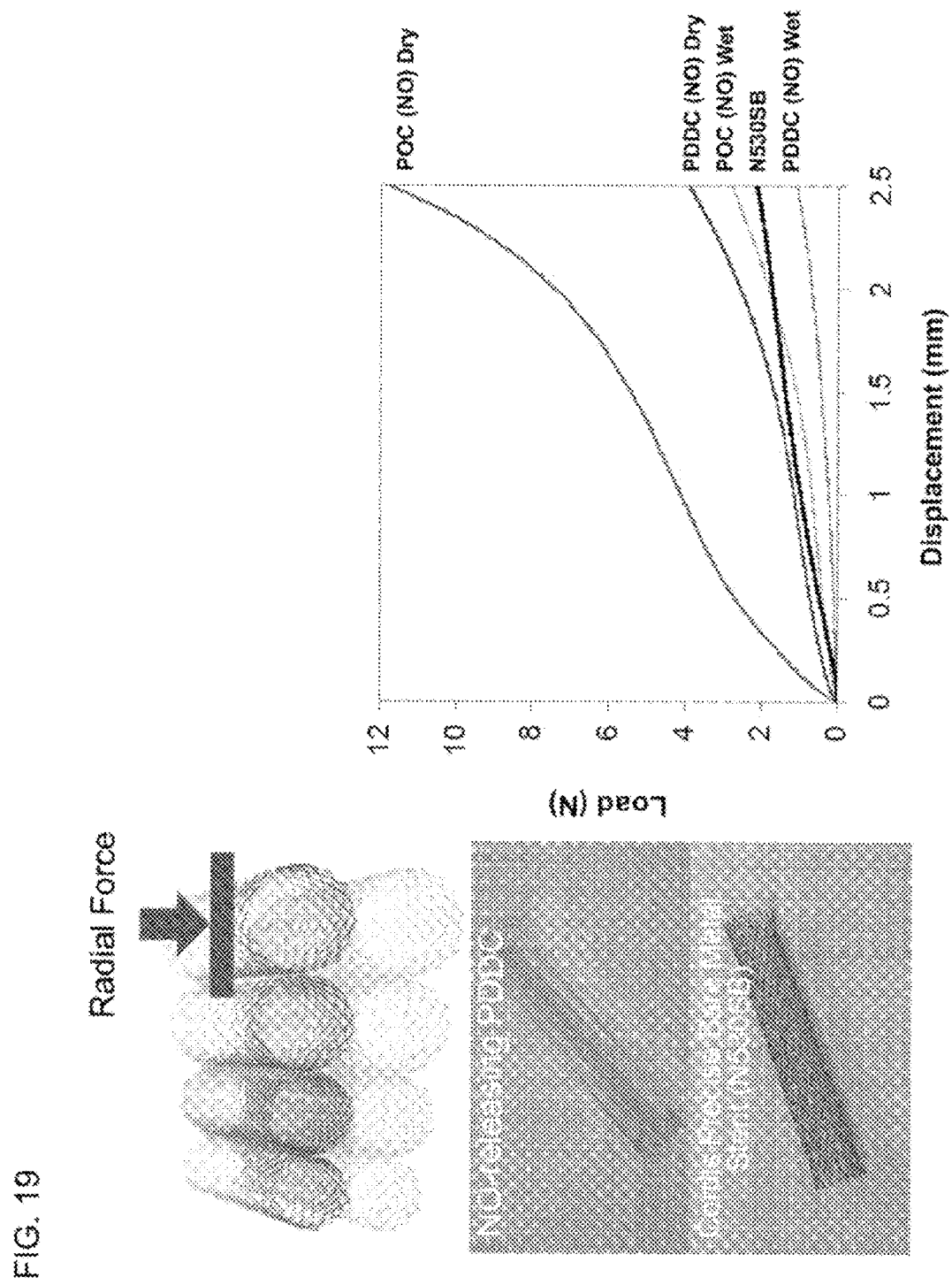
FIG. 19 illustrates the ability of a stent to withstand deformation via radial compression. A wet stent versus a dry stent comprising either POC (NO) or PDDC (NO) were compared in addition to a Cordis brand Precise Bare Metal Stent (N530 SB).

POC (NO) and PDDC (NO) stents were prepared in silicon tubing as described above. The ability of the stents to withstand deformation was measured by applying a radial load to the stent (N) and then measuring displacement (mm). A wet stent versus a dry stent comprising either POC (NO) or PDDC (NO) were compared in addition to a Cordis brand Precise Bare Metal Stent (N530 SB). (See FIG. 19).

Mechanical Properties—Varying Thickness.

Figure 20:
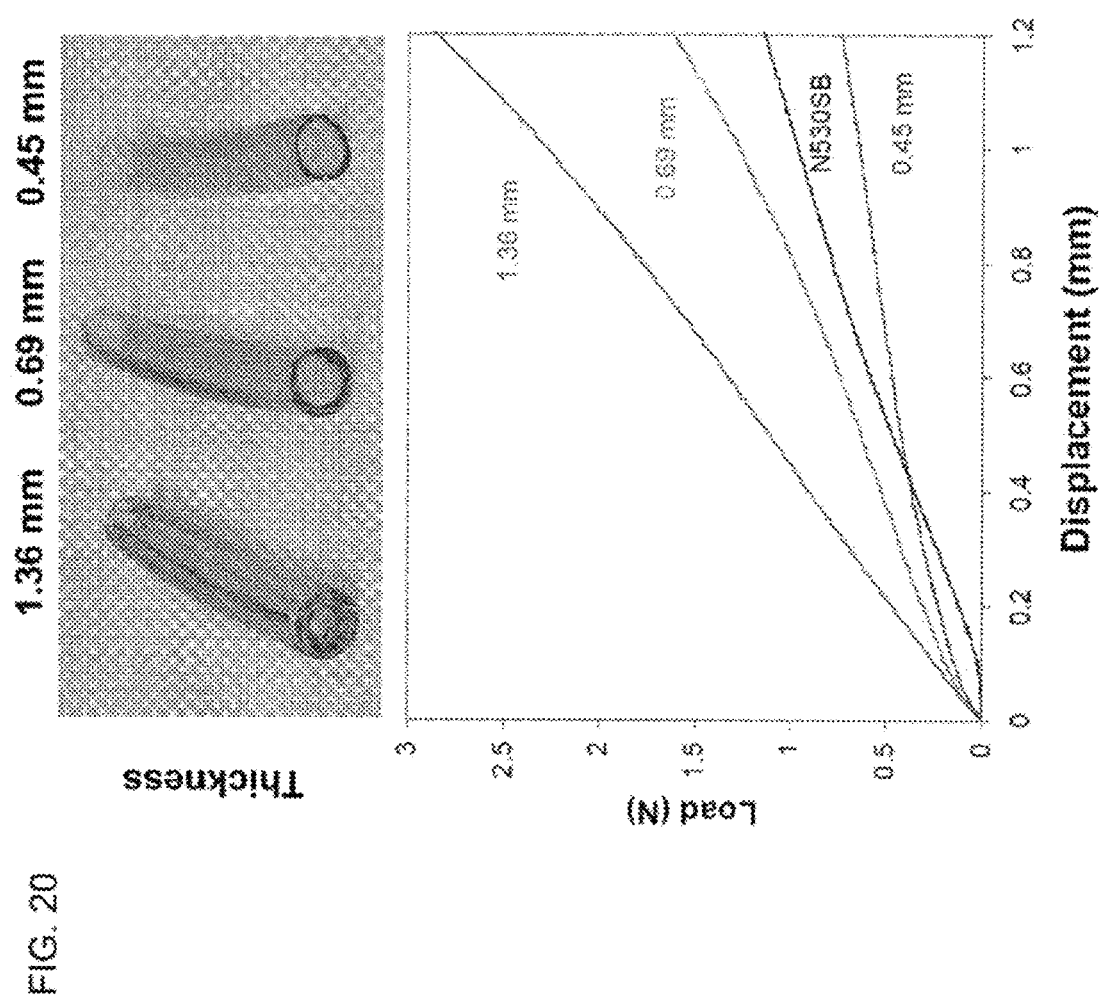
FIG. 20 illustrates the displacement properties of three POC (NO) stents having a diameter of approximately 5 mm and a varying thickness of 0.45 mm, 0.69 mm, or 1.36 mm. A radial load was applied as above and displacement was measured in comparison to a Cordis brand Precise Bare Metal Stent (N530 SB) having a 5 mm diameter and a 0.22 mm thickness as a control.

Three POC (NO) stents were prepared as described above having a diameter of approximately 5 mm and a varying thickness of 0.45 mm, 0.69 mm, or 1.36 mm. A radial load was applied as above and displacement was measured in comparison to a Cordis brand Precise Bare Metal Stent (N530 SB) having a 5 mm diameter and a 0.22 mm thickness as a control. (See FIG. 20). The POC (NO) stents having an approximately 5 mm diameter and a 0.45-0.69 mm thickness resisted deformation similarly as the control stent.

Mechanical Properties—Varying Diameter.

Figure 21:
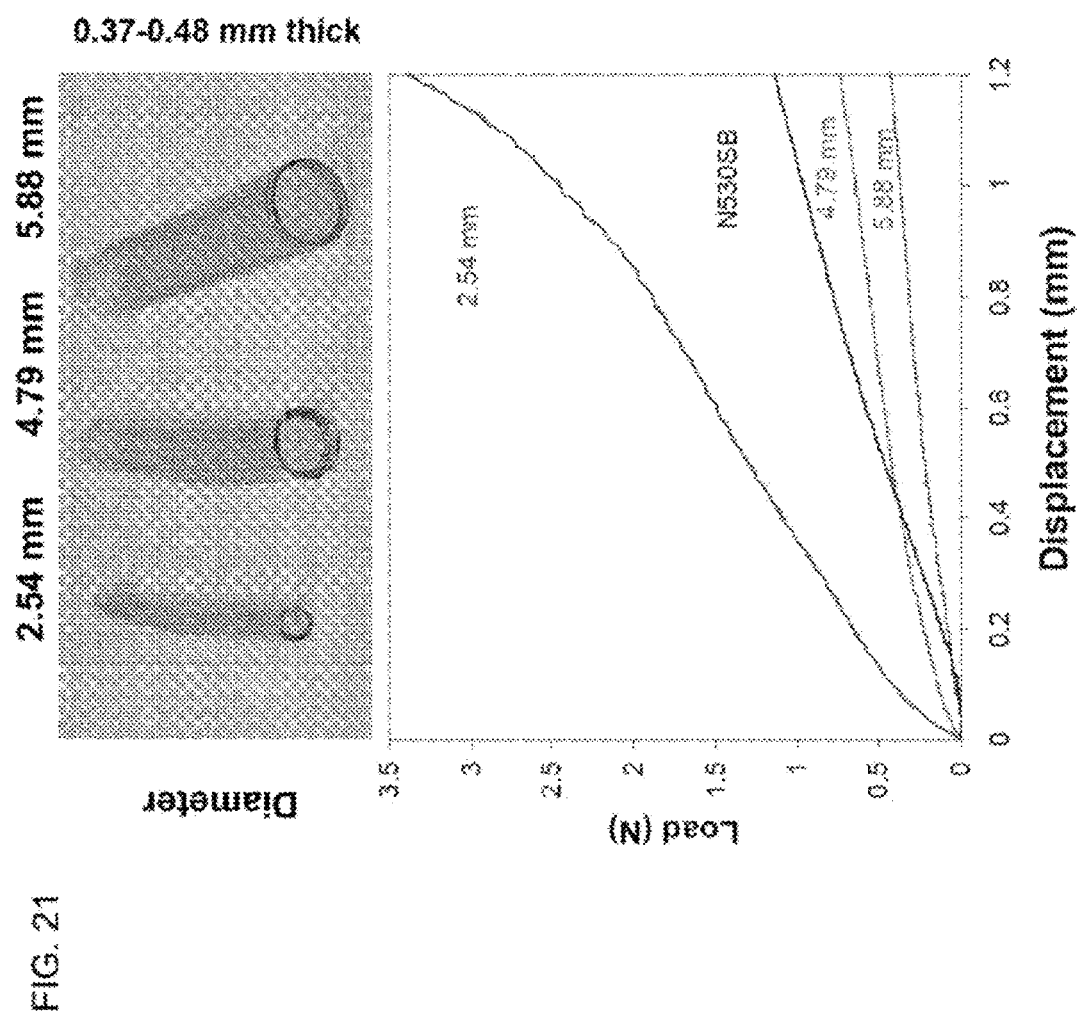
FIG. 21 illustrates the displacement properties of three POC (NO) stents having a varying thickness between 0.37-0.48 mm and diameters of 2.54 mm, 4.79 mm, or 5.88 mm. A radial load was applied as above and displacement was measured in comparison to a Cordis brand Precise Bare Metal Stent (N530 SB) having a 5 mm diameter and a 0.22 mm thickness as a control.

Three POC (NO) stents were prepared as described above having a varying thickness between 0.37-0.48 mm and diameters of 2.54 mm, 4.79 mm, or 5.88 mm. A radial load was applied as above and displacement was measured in comparison to a Cordis brand Precise Bare Metal Stent (N530 SB) having a 5 mm diameter and a 0.22 mm thickness as a control. (See FIG. 21). The POC (NO) stents having diameters of 4.79 mm or 5.88 mm resisted deformation better than the control stent. Based on FIG. 21, it can be extrapolated that a POC (NO) stent having a diameter between 2.54 mm and 4.79 mm will resist deformation similarly to the control stent.

Mechanical Properties—Ability to Resist Bending.

Figure 22:
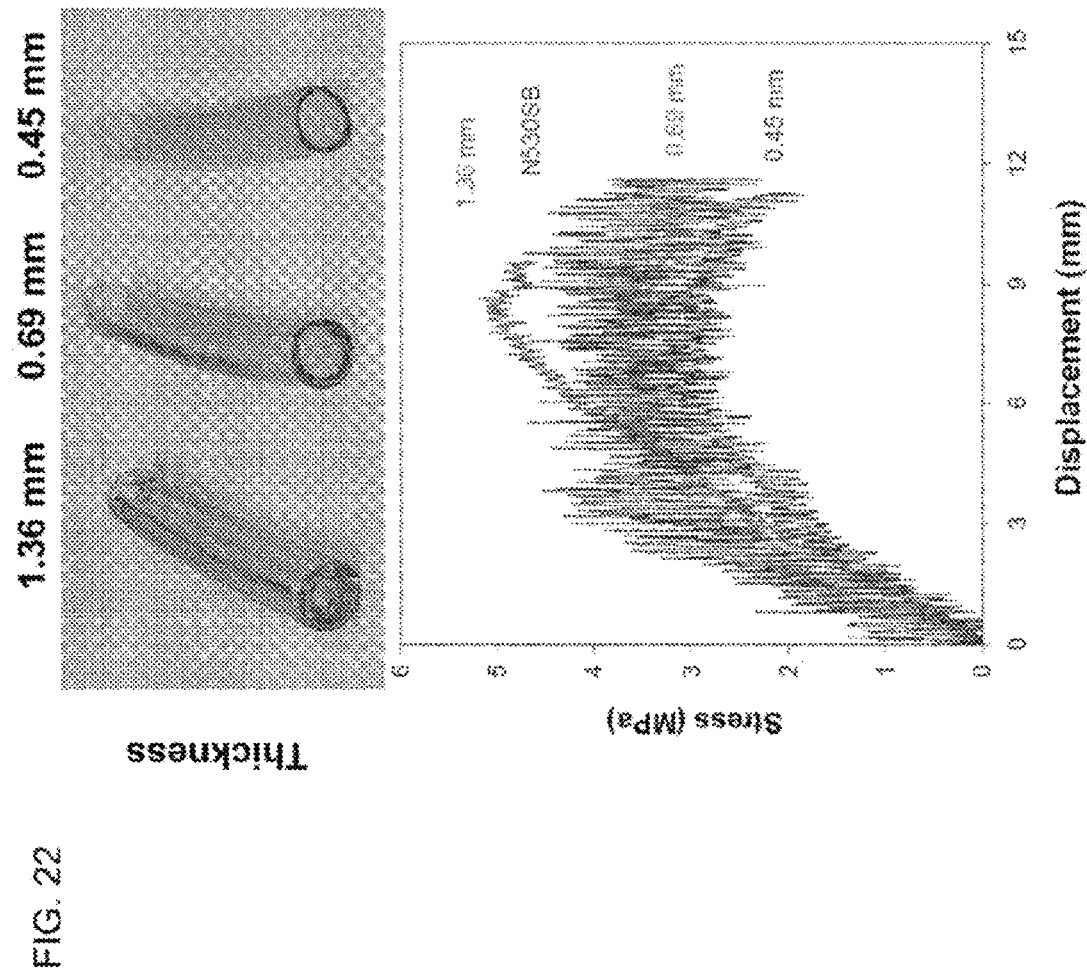
FIG. 22 illustrates the ability of three POC (NO) stents having varying thickness as in FIG. 20 to resist bending in comparison to a Cordis brand Precise Bare Metal Stent (N530 SB) having a 5 mm diameter and a 0.22 mm thickness as a control.
Figure 23:
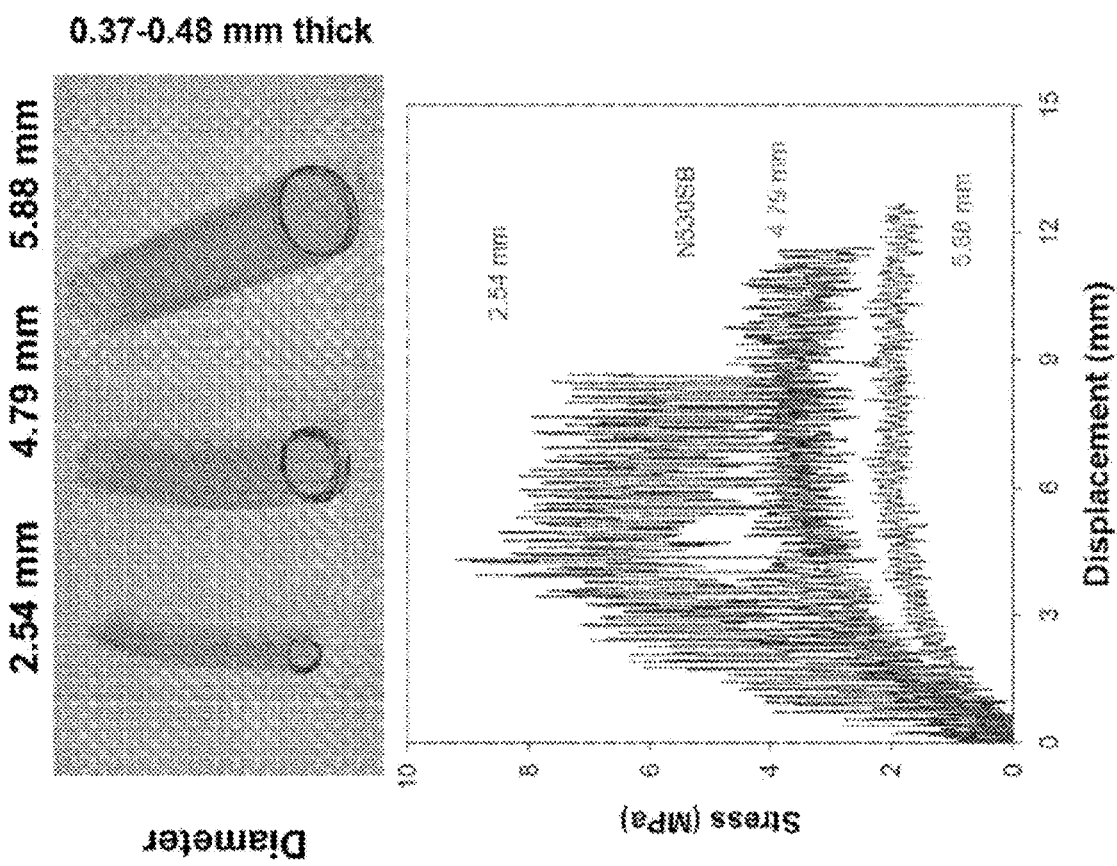
FIG. 23 illustrates the ability of three POC (NO) stents having varying diameter as in FIG. 21 to resist bending in comparison to a Cordis brand Precise Bare Metal Stent (N530 SB) having a 5 mm diameter and a 0.22 mm thickness as a control.

The ability of the six POC (NO) stents described above having varying thickness and varying diameter was measured by determining the amount of force necessary to create a 45 degree angle in the stents in comparison to a Cordis brand Precise Bare Metal Stent (N530 SB) having a 5 mm diameter and a 0.22 mm thickness as a control. (See FIGS. 22 and 23). A POC (NO) stent having a diameter of approximately 5 mm and a thickness of 0.69 mm behaved similarly to the control stent (FIG. 22), as did a POC (NO) stent having a diameter of 4.79 mm and a varying thickness between 0.37-0.48 mm (FIG. 23).

Ability of a Coated Porcine Artery to Withstand Deformation.

Figure 24:
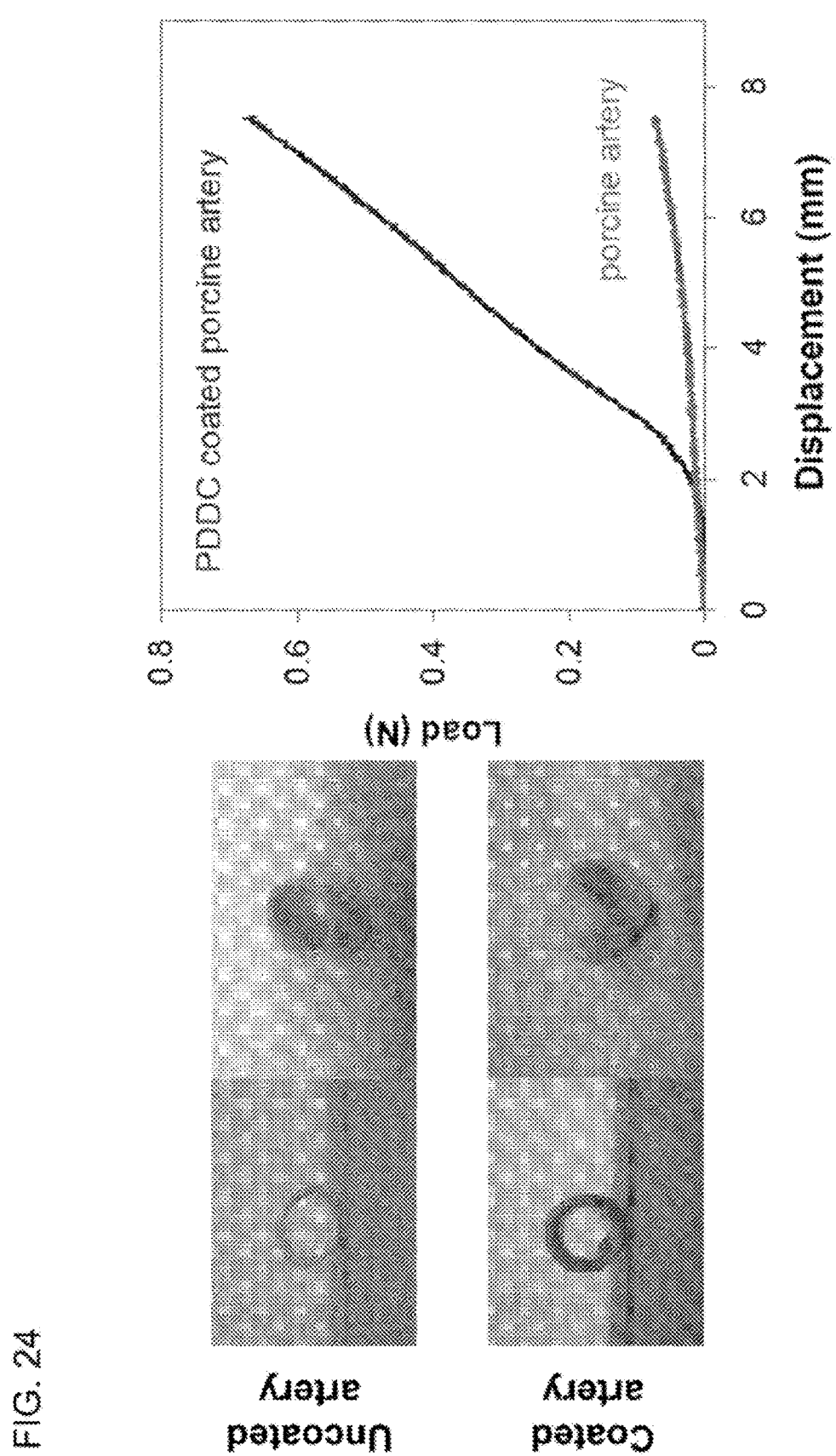
FIG. 24 illustrates the ability of a coated/uncoated porcine arteries to withstand deformation via radial compression.

A PDDC stent was prepared in a porcine artery having a diameter of approximately 15 mm and a thickness of approximately 1.7 mm. The stent had a thickness of approximately 0.8 mm. A radial load was applied to the artery with or without the stem and displacement was measured at room temperature. (See FIG. 24).

REFERENCES

1. Rosamond W, Flegal K, Friday G, Furie K, Go A, Greenlund K, Haase N, Ho M, Howard V, Kissela B, Kittner S, Lloyd-Jones D, McDermott M, Meigs J, Moy C, Nichol G, O'Donnell C J, Roger V, Rumsfeld J, Sorlie P, Steinberger J, Thom T, Wasserthiel-Smoller S, Hong Y. Heart disease and stroke statistics—2007 update: a report from the American Heart Association Statistics Committee and Stroke Statistics Subcommittee. *Circulation* 2007; 115:e69-171.
2. Smith S C, Jr., Dove J T, Jacobs A K, Kennedy J W, Kereiakes D, Kern M J, Kuntz R E, Popma J J, Schaff H V, Williams D O, Gibbons R J, Alpert J P, Eagle K A, Faxon D P, Fuster V, Gardner T J, Gregoratos G, Russell R O, Smith S C, Jr. ACC/AHA guidelines of percutaneous coronary interventions—executive summary. A report of the American College of Cardiology/American Heart Association Task Force on Practice Guidelines. *J. Am Coll Cardiol* 2001; 37:2215-2239.
3. Stone G W, Ellis S G, Cox D A, Hermiller J, O'Shaughnessy C, Mann J T, Turco M, Caputo R, Bergin P, Greenberg J, Popma J J, Russell M E. A polymer-based, paclitaxel-eluting stent in patients with coronary artery disease. *N Engl J Med* 2004; 350:221-231.
4. Unger F, Serruys P W, Yacoub M H, Ilsley C, Paulsen P K, Nielsen T T, Eysmann L, Kiemeneij F. Revascularization in multivessel disease: comparison between two-year outcomes of coronary bypass surgery and stenting. *J Thorac Cardiovasc Surg* 2003; 125:809-820.
5. Lagerqvist B, James S K, Stenestrand U, Lindback J, Nilsson T, Wallentin L. Long-term outcomes with drug-eluting stems versus bare-metal stents in Sweden. *N Engl J Med* 2007; 356:1009-1019.
6. Spaulding C, Daemen J, Boersma E, Cutlip D E, Serruys P W. A pooled analysis of data comparing sirolimus-eluting stems with bare-metal stents. *N Engl J Med* 2007; 356:989-997.
7. Boden W E, O'Rourke R A, Teo K K, Hartigan P M, Maron D J, Kostuk W J, Knudtson M, Dada M, Casperson P, Harris C L, Chaitman B R, Shaw L, Gosselin G, Nawaz S, Title L M, Gau G, Blaustein A S, Booth D C, Bates E R, Spertus J A, Berman D S, Mancini G B, Weintraub W S. Optimal medical therapy with or without PCI for stable coronary disease. *N Engl 0.1 Med* 2007; 356:1503-1516.
8. Clowes A W, Reidy M A, Clowes M M. Mechanisms of stenosis after arterial injury. *Lab Invest* 1983; 49:208-215.
9. Fingerle J, Johnson R, Clowes A W, Majesky M W, Reidy M A. Role of platelets in smooth muscle cell proliferation and migration after vascular injury in rat carotid artery. *Proc Natl Acad Sci USA* 1989; 86:8412-8416.
10. Davies M G, Hagen P O. Pathobiology of intimal hyperplasia. *Br J Surg* 1994; 81:1254-1269.
11. Libby P, Schwartz D, Brogi E, Tanaka H, Clinton S K. A cascade model for restenosis. A special case of atherosclerosis progression. *Circulation* 1992; 86:11147-11152.
12. Lindner V, Lappi D A, Baird A, Majack R A, Reidy M A. Role of basic fibroblast growth factor in vascular lesion formation. *Circ Res* 1991; 68:106-113.
13. Douglas S A, Louden C, Vickery-Clark L M, Storer B L, Hart T, Feuerstein G Z, Elliott J D, Ohlstein E H. A role for endogenous endothelin-1 in neointimal formation after rat carotid artery balloon angioplasty. Protective effects of the novel nonpeptide endothelin receptor antagonist SB 209670. *Circ Res* 1994; 75:190-197.
14. Prescott M F, Webb R L, Reidy M A. Angiotensin-converting enzyme inhibitor versus angiotensin II, AT1 receptor antagonist. Effects on smooth muscle cell migration and proliferation after balloon catheter injury. *Am J Pathol* 1991; 139:1291-1296.
15. Lindner V, Majack R A, Reidy M A. Basic fibroblast growth factor stimulates endothelial regrowth and proliferation in denuded arteries. *J Clin Invest* 1990; 85:2004-2008
16. Kabel E G, Shum L, Pompili V J, Yang Z Y, San H, Shu H B, Liptay S, Gold L, Gordon D, Derynck R, Direct transfer of transforming growth factor beta 1 gene into arteries stimulates fibrocellular hyperplasia. *Proc Natl Acad Sci USA* 1993; 90:10759-10763.
17. Majesky M W, Lindner V, Twardzik D R, Schwartz S M, Reidy M A. Production of transforming growth factor beta 1 during repair of arterial injury. *J Clin Invest* 1991; 88:904-910.
18. Kibbe M, Billiar T, Tzeng E. Inducible nitric oxide synthase and vascular injury. *Cardiovasc Res* 1999; 43:650-657.
19. Vaughn M W, Kuo L, Liao J C. Estimation of nitric oxide production and reaction rates in tissue by use of a mathematical model. *Am J Physiol* 1998; 274:H2163-H2176.
20. Radomski M W, Palmer R M, Moncada S. Endogenous nitric oxide inhibits human platelet adhesion to vascular endothelium. *Lancet* 1987; 2:1057-1058,
21. Kubes P, Suzuki M, Granger D N. Nitric oxide: an endogenous modulator of leukocyte adhesion. *Proc Natl Acad USA* 1991; 88:4651-4655.
22. Kibbe M R, Li J, Nie S, Watkins S C, Lizonova A, Kovesdi I, Simmons R L, Billiar T R, Tzeng E. Inducible nitric oxide synthase (iNOS) expression upregulates p21 and inhibits vascular smooth muscle cell proliferation through p42/44 mitogen-activated protein kinase activation and independent of p53 and cyclic guanosine monophosphate [In Process Citation]. *J Vasc Surg* 2000; 31:1214-1228.
23. Garg U C, Hassid A. Nitric oxide-generating vasodilators and 8-bromo-cyclic guanosine monophosphate inhibit mitogenesis and proliferation of cultured rat vascular smooth muscle cells. *J Clin Invest* 1989; 83:1774-1777.
24. Nishio E, Fukushima K, Shiozaki M, Watanabe Y. Nitric oxide donor SNAP induces apoptosis in smooth muscle cells through cGMP-independent mechanism. *Biochem Biophys Res Commun* 1996; 221:163-168.
25. Tzeng E, Kim Y M, Pitt B R, Lizonova A, Kovesdi I, Billiar T R. Adenoviral transfer of the inducible nitric oxide synthase gene blocks endothelial cell apoptosis. *Surgery* 1997; 122:255-263.
26. Ignarro L J, Buga G M, Wood K S, Byrns R E, Chaudhuri G. Endothelium-derived relaxing factor produced and released from artery and vein is nitric oxide. *Proc Natl Acad Sci USA* 1987; 84:9265-9269.
27. Furchgott R F, Zawadzki J V. The obligatory role of endothelial cells in the relaxation of arterial smooth muscle by acetylcholine. *Nature* 1980; 288:373-376.
28. Davies M G, Dalen H, Kim J H, Barber L, Svendsen E, Hagen P O. Control of accelerated vein graft atheroma with the nitric oxide precursor: L-arginine. *J Surg Res* 1995; 59:35-42.
29. Marks D S, Vita J A, Folts J D, Keaney J F J, Welch G N, Loscalzo J. Inhibition of neointimal proliferation in rabbits after vascular injury by a single treatment with a protein adduct of nitric oxide. *J Clin Invest* 1995; 96:2630-2638.
30. Lee J S, Adrie C, Jacob H J, Roberts J D J, Zapol W M, Bloch K D. Chronic inhalation of nitric oxide inhibits neointimal formation after balloon-induced arterial injury. *Circ Res* 1996; 78:337-342.
31. Kaul S, Cercek B, Rengstrom J, Xu X P, Molloy M D, Dimayuga P, Parikh A K, Fishbein M C, Nilsson J, Rajavashisth T B, Shah P K. Polymeric-based perivascular delivery of a nitric oxide donor inhibits intimal thickening after balloon denudation arterial injury: role of nuclear factor-kappaB. *J Am Coll Cardiol* 2000; 35:493-501.
32. von der Leyen H, Gibbons G H, Morishita R, Lewis N P, Zhang L, Nakajima M, Kaneda Y, Cooke J P, Dzau V J. Gene therapy inhibiting neointimal vascular lesion: in vivo transfer of endothelial cell nitric oxide synthase gene. *Proc Natl Acad Sci USA* 1995; 92:1137-1141.
33. Shears L L, Kibbe M R, Murdock A D, Billiar T R, Lizonova A, Kovesdi I, Watkins S C, Tzeng E. Efficient inhibition of intimal hyperplasia by adenovirus-mediated inducible nitric oxide synthase gene transfer to rats and pigs in vivo. *Journal of the American College of Surgeons* 1998; 187:295-306.
34. Kibbe M R, Tzeng E, Gleixner S L, Watkins S C, Kovesdi I, Lizonova A, Makaroun M S, Billiar T R, Rhee R Y. Adenovirus-mediated gene transfer of human inducible nitric oxide synthase in porcine vein grafts inhibits intimal hyperplasia. *J Vasc Surg* 2001; 34:156-165.
35. Bohl K S, West J L. Nitric oxide-generating polymers reduce platelet adhesion and smooth muscle cell proliferation. *Biomaterials* 2000; 21:2273-2278.

36. Kown M H, Yamaguchi A, Jahncke C L, Miniati D, Murata S, Grunenfelder J, Koransky M L, Rothbard J B, Robbins R C. L-arginine polymers inhibit the development of vein graft neointimal hyperplasia. *J Thorac Cardiovasc Surg* 2001; 121:971-980.

37. Chaux A, Ruan X M, Fishbein M C, Ouyang Y, Kaul S, Pass J A, Matloff J M. Perivascular delivery of a nitric oxide donor inhibits neointimal hyperplasia in vein grafts implanted in the arterial circulation. *J Thorac Cardiovasc Surg* 1998; 115:604-612.

38. Fleser P S, Nuthakki V K, Malinzak L E, Callahan R E, Seymour M L, Reynolds M M, Merz S I, Meyerhoff M E, Bendick P J, Zelenock G B, Shanley C J. Nitric oxide-releasing biopolymers inhibit thrombus formation in a sheep model of arteriovenous bridge grafts. *J Vasc Surg* 2004; 40:803-811.

39. Pearce C G, Najjar S F, Kapadia M R, Murar J, Eng J, Lyle B, Aalami O O, Jiang Q, Hrabie J A, Saavedra J E, Keefer L K, Kibbe M R. Beneficial effect of a short-acting NO donor for the prevention of neointimal hyperplasia. *Free Radic Biol Med* 2008; 44:73-81.

40. Kapadia M R, Chow L W, Tsihlis N D, Ahanchi S S, Eng J W, Murar J, Martinez J, Popowich D A, Jiang Q, Hrabie J A, Saavedra J E, Keefer L K, Hulvat J F, Stupp S I, Kibbe M R. Nitric oxide and nanotechnology: a novel approach to inhibit neointimal hyperplasia. *J Vasc Surg* 2008; 47:173-182.

41. Fishbein I, Alferiev I, Bakay M, Stachelek S J, Sobolewski P, Lai M, Choi H, Chen I W, Levy R J. Local delivery of gene vectors from bare-metal stents by use of a biodegradable synthetic complex inhibits in-stent restenosis in rat carotid arteries. *Circulation* 2008; 117:2096-2103.

42. Hrabie J A, Keefer L K. Chemistry of the nitric oxide-releasing diazeniumdiolate ("nitrosohydroxylamine") functional group and its oxygen-substituted derivatives. *Chem Rev* 2002; 102:1135-1154.

43. Yoon J H, Wu C J, Homme J, Tuch R J, Wolff R G, Topol E J, Lincoff A M. Local delivery of nitric oxide from an eluting stent to inhibit neointimal thickening in a porcine coronary injury model. *Yonsei Med J* 2002; 43:242-251.

44. Hou D, Narciso H, Kamdar K, Zhang P, Barclay B, March K L. Stent-based nitric oxide delivery reducing neointimal proliferation in a porcine carotid overstretch injury model. *Cardiovasc Intervent Radiol* 2005; 28:60-65.

45. Zhang H, Annich G M, Miskulin J, Osterholzer K, Merz S I, Bartlett R H, Meyerhoff M E. Nitric oxide releasing silicone rubbers with improved blood compatibility: preparation, characterization, and in vivo evaluation. *Biomaterials* 2002; 23:1485-1494.

46. Frost M C, Rudich S M, Zhang H, Maraschio M A, Meyerhoff M E. In vivo biocompatibility and analytical performance of intravascular amperometric oxygen sensors prepared with improved nitric oxide-releasing silicone rubber coating. *Anal Chem* 2002; 74:5942-5947.

47. Smith D J, Chakravarthy D, Pulfer S, Simmons M L, Hrabie J A, Citro M L, Saavedra J E, Davies K M, Hutsell T C, Mooradian D L, Hanson S R, Keefer L K. Nitric oxide-releasing polymers containing the [N(O)NO]— group. *J Med Chem* 1996; 39:1148-1156.

48. Puller S K, Ott D, Smith D J. Incorporation of nitric oxide-releasing crosslinked polyethyleneimine microspheres into vascular grafts. *J Biomed Mater Res* 1997; 37:182-189.

49. Iakovou I, Schmidt T, Bonizzoni E, Ge L, Sangiorgi G M, Stankovic G, Airoldi F, Chieffo A, Montorfano M, Carlino M, Michev I, Corvaja N, Briguori C, Gerckens U, Grube E, Colombo A. Incidence, predictors, and outcome of thrombosis after successful implantation of drug-eluting stents. *JAMA* 2005; 293:2126-2130.

50. Spaulding C, Daemen J, Boersma E, Cutlip D E, Serruys P W. A pooled analysis of data comparing sirolimus-eluting stents with bare-metal stents. *N Engl J Med* 2007; 356:989-997.

51. Lagerqvist B, James S K, Stenestrand U, Lindback J, Nilsson T, Wallentin L. Long-term outcomes with drug-eluting stents versus bare-metal stents in Sweden. *N Engl J Med* 2007; 356:1009-1019.

52. Maisel W H. Unanswered questions—drug-eluting stents and the risk of late thrombosis. *N Engl J Med* 2007; 356:981-984.

53. Finn A V, Joner M, Nakazawa G, Kolodgie F, Newell J, John M C, Gold H K, Virmani R. Pathological correlates of late drug-eluting stent thrombosis: strut coverage as a marker of endothelialization. *Circulation* 2007; 115:2435-2441.

54. Stack R S, Califf R M, Phillips H R, Pryor D B, Quigley P J, Bauman R P, Tcheng J E, Greenfield J C, Jr. Interventional cardiac catheterization at Duke Medical Center. *Am J Cardiol* 1988; 62:3F-24F.

55. Tamai H, Igaki K, Kyo E, Kosuga K, Kawashima A, Matsui S, Komori H, Tsuji T, Motohara S, Uehata H. Initial and 6-month results of biodegradable poly-1-lactic acid coronary stents in humans. *Circulation* 2000; 102:399-404.

56. Commandeur S, van Beusekom H M, van der Giessen W J. Polymers, drug release, and drug-eluting stems. *J Interv Cardiol* 2006; 19:500-506.

57. van der Giessen W J, Lincoff A M, Schwartz R S, van Beusekom H M, Serruys P W, Holmes D R, Jr., Ellis S G, Topol E J. Marked inflammatory sequelae to implantation of biodegradable and nonbiodegradable polymers in porcine coronary arteries. *Circulation* 1996; 94:1690-1697.

58. Yang J, Webb A R, Pickerill S J, Hageman G, Ameer G A. Synthesis and evaluation of poly(diol citrate) biodegradable elastomers. *Biomaterials* 2006; 27:1889-1898.

59. Yang J, Motlagh D, Webb A R, Ameer G A. Novel biphasic elastomeric scaffold for small-diameter blood vessel tissue engineering. *Tissue Eng* 2005; 11:1876-1886.

60. Yang J, Motlagh D, Allen J B, Webb A R, Kibbe M R, Aalami O, Kapadia M, Carroll T J, Ameer G A. Modulating Expanded Polytetrafluoroethylene Vascular Graft Host Response via Citric Acid-Based Biodegradable Elastomers. *Adv Mater* 2006; 18:1493-1498.

61. Motlagh D, Yang J, Lui K Y, Webb A R, Ameer G A. Hemocompatibility evaluation of poly(glycerol-sebacate) in vitro for vascular tissue engineering. *Biomaterials* 2006; 27:4315-4324.

62. Tamada Y, Kulik E A, Ikada Y. Simple method for platelet counting. *Biomaterials* 1995; 16:259-261.

63. Anseth K S, Metters A T, Bryant S J, Martens P J, ElisSeeff J H, Bowman C N. In situ forming degradable networks and their application in tissue engineering and drug delivery. *J Control Release* 2002; 78:199-209.

64. Burdick J A, Peterson A J, Anseth K S. Conversion and temperature profiles during the photoinitiated polymerization of thick orthopaedic biomaterials. *Biomaterials* 2001; 22:1779-1786.

65. Rydholm A E, Bowman C N, Anseth K S. Degradable thiol-acrylate photopolymers: polymerization and degradation behavior of an in situ forming biomaterial. *Biomaterials* 2005; 26:4495-4506.

66. Simms H M, Bowman C M, Anseth K S. Using living radical polymerization to enable facile incorporation of materials in microfluidic cell culture devices. *Biomaterials* 2008; 29:2228-2236.
67. Reisman M, Shuman B J, Harms V. Analysis of heat generation during rotational atherectomy using different operational techniques. *Cather Cardiovasc Diagn* 1998; 44:453-455.
68. Yang J, Motlagh D, Webb A R, Ameer G A. Novel biphasic elastomeric scaffold for small-diameter blood vessel tissue engineering. *Tissue Eng* 2005; 11:1876-1886.
69. Dyet J F, Watts W G, Ettles D F, Nicholson A A. Mechanical properties of metallic stents: how do these properties influence the choice of stent for specific lesions? *Cardiovasc Intervent Radiol* 2000; 23:47-54.
70. Nikanorov A, Smouse H B, Osman K, Bialas M, Shrivastava S, Schwartz L B. Fracture of self-expanding nitinol stents stressed in vitro under simulated intravascular conditions. *J Vasc Surg* 2008; 48:435-440.
71. Chen M C, Tsai H W, Chang Y, Lai W Y, Mi F L, Liu C T, Wong H S, Sung H W. Rapidly self-expandable polymeric stents with a shape-memory property. *Biomacromolecules* 2007; 8:2774-2780.
72. Kibbe M R, Nie S, Yoneyama T, Hatakeyama K, Lizonova A, Kovesdi I, Billiar T R, Tzeng E. Optimization of ex vivo inducible nitric oxide synthase gene transfer to vein grafts. *Surgery* 1999; 126:323-329.
73. Webb A R, Macrie B D, Ray A S, Russo J E, Siegel A M, Glucksberg M R, Ameer G A. In vitro characterization of a compliant biodegradable scaffold with a novel bioreactor system. *Ann Biomed Eng* 2007; 35:1357-1367.
74. Gunther S, Alexander R W, Atkinson W J, Gimbrone M A. Functional angiotensin-li receptors in cultured vascular smooth-muscle cells. *J Cell Biol* 1982; 92:289-298.
75. Mahabaleshwar G H, Somanath P R, Byzova T V. Methods for Isolation for Endothelial and Smooth Muscle Cells and In Vitro Proliferation Assays. In: *Cardiovascular Disease, Volume 2: Molecular Medicine.* 2006:197-208.
76. Allen J, Khan S, Serrano M C, Ameer G. Characterization of Porcine Circulating Progenitor Cells: Toward a Functional Endothelium. Tissue Eng 2008.

In the foregoing description, certain terms have been used for brevity, clearness, and understanding. No unnecessary limitations are to be implied therefrom beyond the requirement of the prior art because such terms are used for descriptive purposes and are intended to be broadly construed. The different compositions and method steps described herein may be used alone or in combination with other compositions and method steps. It is to be expected that various equivalents, alternatives and modifications are possible. The cited patent and non-patent references are incorporated by reference in their entireties. In the event that a definition provided in the present disclosure conflicts with a definition provided in a cited reference, the definition provided in the present disclosure supersedes the definition for the term provided in the cited reference.

We claim:

1. A liquid cast biodegradable arterial stent, wherein the stent comprises a biodegradable polymer and the stent is formed by curing in situ a solution comprising prepolymers or monomers that polymerize or cross-link to form the biodegradable polymer.

2. The stein of claim 1, wherein the stent comprises an agent for inhibiting neointimal hyperplasia or thrombosis.

3. The stent of claim 1, wherein the biodegradable polymer is formed from a prepolymer formed by reacting a mixture comprising a tricarboxylic acid and an alkane diol.

4. The stent of claim 3, wherein the tricarboxylic acid is citric acid.

5. The stent of claim 3, wherein the alkane diol is a C6-C14 alkane diol.

6. The stent of claim 3, wherein the prepolymer further is functionalized via reacting the prepolymer with a compound providing a crosslinkable amine group or a crosslinkable acrylate group.

7. The stent of claim 3, wherein the prepolymer further is acrylated at one or more hydroxyl groups.

8. The stent of claim 3, wherein the biodegradable polymer is formed by subjecting the prepolymer to cross-linking.

9. The stent of claim 8, wherein the cross-linking is achieved by exposing the prepolymer to light or heat.

10. The stem of claim 1, wherein the stent releases an agent that inhibits neointimal hyperplasia or thrombosis.

* * * * *

UNITED STATES PATENT AND TRADEMARK OFFICE
CERTIFICATE OF CORRECTION

PATENT NO. : 9,801,738 B2
APPLICATION NO. : 13/641378
DATED : October 31, 2017
INVENTOR(S) : Melina R. Kibbe and Guillermo A. Ameer Page 1 of 1

It is certified that error appears in the above-identified patent and that said Letters Patent is hereby corrected as shown below:

In the Claims

Column 32, Line 22 Claim 2, "stein" should be replaced with "stent".

Column 32, Line 41 Claim 10, "stem" should be replaced with "stent".

Signed and Sealed this
Nineteenth Day of December, 2017

Joseph Matal
*Performing the Functions and Duties of the*
*Under Secretary of Commerce for Intellectual Property and*
*Director of the United States Patent and Trademark Office*